US007264953B2

(12) United States Patent
Lawrence et al.

(10) Patent No.: US 7,264,953 B2
(45) Date of Patent: Sep. 4, 2007

(54) MUTANT PROTEINASE-INHIBITORS AND USES THEREOF

(75) Inventors: Daniel A. Lawrence, Derwood, MD (US); Natalia Gorlatova, Rockville, MD (US); David L. Crandall, Doylestown, PA (US)

(73) Assignees: American National Red Cross, Falls Church, VA (US); Wyeth, Madison, NJ (US)

( * ) Notice: Subject to any disclaimer, the term of this patent is extended or adjusted under 35 U.S.C. 154(b) by 913 days.

(21) Appl. No.: 10/197,258

(22) Filed: Jul. 18, 2002

(65) Prior Publication Data

US 2004/0014190 A1 Jan. 22, 2004

Related U.S. Application Data

(60) Provisional application No. 60/305,908, filed on Jul. 18, 2001, now abandoned.

(51) Int. Cl.
*C12N 9/99* (2006.01)

(52) U.S. Cl. ...................................................... 435/184

(58) Field of Classification Search ................. 435/184
See application file for complete search history.

(56) References Cited

U.S. PATENT DOCUMENTS 6,103,498 A * 8/2000 Lawrence et al. ......... 435/69.2
6,489,143 B1 12/2002 Lawrence et al.

OTHER PUBLICATIONS

International Search Report of PCT/US02/22822.

Lawrence et al., "Serpin Reactive Center Loop Mobility is Required for Inhibitor Function but Not for Enzyme Recognition," *The Journal of Biological Chemistry* (Nov. 4, 1994), vol. 269, No. 44. pp. 27657-27662.

Berkenpas et al., "Molecular evolution of plasminogen activator inhibitor-1 functional stability," *The EMBO Journal* (1995), vol. 14, No. 13, pp. 2969-2977.

Debrock et al., "Neutralization of plasminogen activator inhibitor-1 inhibitory properties: identification of two different mechanisms," *Biochimica et Biophysica Acta* (1997), vol. 1337, pp. 257-266.

Debrock et al., "Cloning of a singing-chain variable fragment (scFv) switching active plasminogen activator inhibitor-1 to substrate," *Gene* (1997), vol. 189, pp. 83-88.

Doolittle, "Angiotensinogen Is Related to the Antitrypsin-Antithrombin-Ovalbumin Family," *Science* (Oct. 28, 1983), vol. 222, pp. 417-419.

Eitzman et al., "Peptide-Mediated Inactivation of Recombinant and Platelet Plasminogen Activator Inhibitor-1 In Vitro," *J. Clin. Invest.* (May 1995), vol. 95, pp. 2416-2420.

Fay et al., "Platelets Inhibit Febrinolysis In Vitro by Both Plasminogen Activator Inhibitor-1 Dependent and -Independent Mechanisms," *Blood* (Jan. 15, 1994), vol. 83, 351-356.

Ginsburg et al., "cDNA Cloning of Human Plasminogen Activator-Inhibitor from Endothelial Cells," *J. Clin. Invest.* (Dec. 1986), vol. 78, pp. 1673-1680.

Huber et al., "Implications of the Three-Dimensional Structure of $\alpha_1$-Aantitrypsin for Structure and Function of Serpins," *Biochemistry* (Nov. 14, 1989), vol. 28, No. 23, pp. 8951-8966.

Kvassman et al., "The Acid Stabilization of Plasminogen Activator Inhibitor-1 Depends on Protonation of a Single Group That Affects Loop Insertion into β-Sheet A," *The Journal of Biological Chemistry* (Nov. 17, 1995), vol. 270, No. 46, pp. 27942-27947.

Lawrence et al., "Purification of active human plasminogen activator inhibitor 1 from *Escherichia coli,*" *Eur. J. Biochem.* (1989), vol. 186, pp. 523-533.

Lawrence et al., "Structure-Function Studies of the SERPIN Plasminogen Activator Inhibitor Type 1," *The Journal of Biological Chemistry* (Nov. 25, 1990), vol. 265, No. 33, pp. 20293-20301.

Lawrence et al., "Serpin-Protease Complexes Are Trapped as Stable Acyl-Enzyme Intermediates," *The Journal of Biological Chemistry* (Oct. 27, 1995), vol. 270, No. 43, pp. 25309-25312.

Lawrence et al., "Localization of Vitronection Binding Domain in Plasminogen Activator Inhibitor 1," *The Journal of Biological Chemistry* (May 27, 1994), vol. 269, No. 21, pp. 15223-15228.

Levi et al., "Inhibition of Plasminogen Activator Inhibitor-1 Activity Results in Pormotion of Endogenous Thrombolysis and Inhibition of Thrombus Extension in Models of Experimental Thrombosis," *Circulation* (Jan. 1992), vol. 85, No. 1, pp. 305-312.

Lobermann et al., "Human $\alpha_1$-Proteianse Inhibitor," *J. Mol. Biol.* (1984), vol. 177, pp. 531-556.

Loskutoff et al., "Detection of an unusually stable fibrinolytic inhibitor produced by bovine endothelial cells," *Proc. Natl. Acad. Sci.* (May 1983), vol. 80, pp. 2956-2960.

Ny et al., "Cloning and Sequence of a cDNA coding for the human β-migrating endothelial-cell-type plasminogen activator inhibitor," *Proc. Natl. Acad. Sci.* (Sep. 1986), vol. 83, pp. 6776-6780.

Olson et al., "Role of the Catalytic Serine in the Interactions of Serine Proteinases with Protein Inhibitors of the Serpin Family," *The Journal of Biological Chemistry* (Dec. 15, 1995), vol. 270, No. 50, pp. 30007-30017.

Sherman et al., "Saturation Mutagenesis of the Plasminogen Activator Inhibitor-1 Reactive Center," *The Journal of Biological Chemistry* (Apr. 15, 1992), vol. 267, No. 11, pp. 7588-7595.

Sherman et al., "Identification of Tissue-type Plasminogen Activator-specific Plasminogen Activator Inhibitor-1 Mutants," *The Journal of Biological Chemistry* (Apr. 21, 1995), vol. 270, No. 16, pp. 9301-9306.

Shubeita et al., "Mutational and Immunochemical Analysis of Plasminogen Activator Inhibitor 1,", *The Journal of Biological Chemistry* (Oct. 25, 1990), vol. 265, No. 30, pp. 18379-18385.

Van Mourik et al., "Purification of an Inhibitor of Plasminogen Activator (Antiactivator) Synthesized by Endothelial Cells," *The Journal of Biological Chemistry* (Dec. 10, 1984), vol. 259, No. 23, pp. 14914-14921.

* cited by examiner

*Primary Examiner*—Bruce R. Campell
*Assistant Examiner*—Roy Teller
(74) *Attorney, Agent, or Firm*—Foley & Lardner LLP

(57) ABSTRACT

A library of mutants of metastable proteins, such as proteinase inhibitors, can be screened for the specific loss of a wild-type capability to bind an antibody, yielding valuable drug-design information which otherwise is unavailable. By this approach, for example, a mutant proteinase inhibitor can be obtained that has the amino acid sequence of a wild-type protein, or an active fragment thereof, save for the presence of one or more mutations in at least one epitope, thereby altering interaction of the mutant with an anti-proteinase inhibitor antibody.

4 Claims, 9 Drawing Sheets

```
         GAATTCCTGCAGCTCAGCAGCCGCCGCCAGAGCAGGACGAACCGCCAATCGCAAGGCACC
       1 ---------+---------+---------+---------+---------+---------+ 60
         CTTAAGGACGTCGAGTCGTCGGCGGCGGTCTCGTCCTGCTTGGCGGTTAGCGTTCCGTGG

         TCTGAGAACTTCAGGATGCAGATGTCTCCAGCCCTCACCTGCCTAGTCCTGGGCCTGGCC
      61 ---------+---------+---------+---------+---------+---------+ 120
         AGACTCTTGAAGTCCTACGTCTACAGAGGTCGGGAGTGGACGGATCAGGACCCGGACCGG
aa                       M  Q  M  S  P  A  L  T  C  L  V  L  G  L  A  -
                        |Signal Peptide
         CTTGTCTTTGGTGAAGGGTCTGCTGTGCACCATCCCCCATCCTACGTGGCCCACCTGGCC
     121 ---------+---------+---------+---------+---------+---------+ 180
         GAACAGAAACCACTTCCCAGACGACACGTGGTAGGGGGTAGGATGCACCGGGTGGACCGG
aa       L  V  F  G  E  G  S  A |V  H  H  P  P  S  Y  V  A  H  L  A  12
                                    Start Mature Protein
         TCAGACTTCGGGGTGAGGGTGTTTCAGCAGGTGGCGCAGGCCTCCAAGGACCGCAACGTG
     181 ---------+---------+---------+---------+---------+---------+ 240
         AGTCTGAAGCCCCACTCCCACAAAGTCGTCCACCGCGTCCGGAGGTTCCTGGCGTTGCAC
aa       S  D  F  G  V  R  V  F  Q  Q  V  A  Q  A  S  K  D  R  N  V  32

         GTTTTCTCACCCTATGGGGTGGCCTCGGTGTTGGCCATGCTCCAGCTGACAACAGGAGGA
     241 ---------+---------+---------+---------+---------+---------+ 300
         CAAAAGAGTGGGATACCCCACCGGAGCCACAACCGGTACGAGGTCGACTGTTGTCCTCCT
aa       V  F  S  P  Y  G  V  A  S  V  L  A  M  L  Q  L  T  T  G  G  52

         GAAACCCAGCAGCAGATTCAAGCAGCTATGGGATTCAAGATTGATGACAAGGGCATGGCC
     301 ---------+---------+---------+---------+---------+---------+ 360
         CTTTGGGTCGTCGTCTAAGTTCGTCGATACCCTAAGTTCTAACTACTGTTCCCGTACCGG
aa       E  T  Q  Q  Q  I  Q  A  A  M  G  F  K  I  D  D  K  G  M  A  72

         CCCGCCCTCCGGCATCTGTACAAGGAGCTCATGGGGCCATGGAACAAGGATGAGATCAGC
     361 ---------+---------+---------+---------+---------+---------+ 420
         GGGCGGGAGGCCGTAGACATGTTCCTCGAGTACCCCGGTACCTTGTTCCTACTCTAGTCG
aa       P  A  L  R  H  L  Y  K  E  L  M  G  P  W  N  K  D  E  I  S  92

         ACCACAGACGCGATCTTCGTCCAGCGGGATCTGAAGCTGGTCCAGGGCTTCATGCCCCAC
     421 ---------+---------+---------+---------+---------+---------+ 480
         TGGTGTCTGCGCTAGAAGCAGGTCGCCCTAGACTTCGACCAGGTCCCGAAGTACGGGGTG
aa       T  T  D  A  I  F  V  Q  R  D  L  K  L  V  Q  G  F  M  P  H  112
         TTCTTCAGGCTGTTCCGGAGCACGGTCAAGCAAGTGGACTTTTCAGAGGTGGAGAGAGCC
     481 ---------+---------+---------+---------+---------+---------+ 540
         AAGAAGTCCGACAAGGCCTCGTGCCAGTTCGTTCACCTGAAAAGTCTCCACCTCTCTCGG
aa       F  F  R  L  F  R  S  T  V  K  Q  V  D  F  S  E  V  E  R  A  132

         AGATTCATCATCAATGACTGGGTGAAGACACACACAAAAGGTATGATCAGCAACTTGCTT
     541 ---------+---------+---------+---------+---------+---------+ 600
         TCTAAGTAGTAGTTACTGACCCACTTCTGTGTGTGTTTTCCATACTAGTCGTTGAACGAA
aa       R  F  I  I  N  D  W  V  K  T  H  T  K  G  M  I  S  N  L  L  152
```

FIGURE 1A

```
           GGGAAAGGAGCCGTGGACCAGCTGACACGGCTGGTGCTGGTGAATGCCCTCTACTTCAAC
     601 ---------+---------+---------+---------+---------+---------+ 660
           CCCTTTCCTCGGCACCTGGTCGACTGTGCCGACCACGACCACTTACGGGAGATGAAGTTG
aa         G  K  G  A  V  D  Q  L  T  R  L  V  L  V  N  A  L  Y  F  N  172

           GGCCAGTGGAAGACTCCCTTCCCCGACTCCAGCACCCACCGCCGCCTCTTCCACAAATCA
     661 ---------+---------+---------+---------+---------+---------+ 720
           CCGGTCACCTTCTGAGGGAAGGGGCTGAGGTCGTGGGTGGCGGCGGAGAAGGTGTTTAGT
aa         G  Q  W  K  T  P  F  P  D  S  S  T  H  R  R  L  F  H  K  S  192

           GACGGCAGCACTGTCTCTGTGCCCATGATGGCTCAGACCAACAAGTTCAACTATACTGAG
     721 ---------+---------+---------+---------+---------+---------+ 780
           CTGCCGTCGTGACAGAGACACGGGTACTACCGAGTCTGGTTGTTCAAGTTGATATGACTC
aa         D  G  S  T  V  S  V  P  M  M  A  Q  T  N  K  F  N  Y  T  E  212

           TTCACCACGCCCGATGGCCATTACTACGACATCCTGGAACTGCCCTACCACGGGGACACC
     781 ---------+---------+---------+---------+---------+---------+ 840
           AAGTGGTGCGGGCTACCGGTAATGATGCTGTAGGACCTTGACGGGATGGTGCCCCTGTGG
aa         F  T  T  P  D  G  H  Y  Y  D  I  L  E  L  P  Y  H  G  D  T  232

           CTCAGCATGTTCATTGCTGCCCCTTATGAAAAAGAGGTGCCTCTCTCTGCCCTCACCAAC
     841 ---------+---------+---------+---------+---------+---------+ 900
           GAGTCGTACAAGTAACGACGGGGAATACTTTTTCTCCACGGAGAGAGACGGGAGTGGTTG
aa         L  S  M  F  I  A  A  P  Y  E  K  E  V  P  L  S  A  L  T  N  252

           ATTCTGAGTGCCCAGCTCATCAGCCACTGGAAAGGCAACATGACCAGGCTGCCCCGCCTC
     901 ---------+---------+---------+---------+---------+---------+ 960
           TAAGACTCACGGGTCGAGTAGTCGGTGACCTTTCCGTTGTACTGGTCCGACGGGGCGGAG
aa         I  L  S  A  Q  L  I  S  H  W  K  G  N  M  T  R  L  P  R  L  272

           CTGGTTCTGCCCAAGTTCTCCCTGGAGACTGAAGTCGACCTCAGGAAGCCCCTAGAGAAC
     961 ---------+---------+---------+---------+---------+---------+ 1020
           GACCAAGACGGGTTCAAGAGGGACCTCTGACTTCAGCTGGAGTCCTTCGGGGATCTCTTG
aa         L  V  L  P  K  F  S  L  E  T  E  V  D  L  R  K  P  L  E  N  292

           CTGGGAATGACCGACATGTTCAGACAGTTTCAGGCTGACTTCACGAGTCTTTCAGACCAA
    1021 ---------+---------+---------+---------+---------+---------+ 1080
           GACCCTTACTGGCTGTACAAGTCTGTCAAAGTCCGACTGAAGTGCTCAGAAAGTCTGGTT
aa         L  G  M  T  D  M  F  R  Q  F  Q  A  D  F  T  S  L  S  D  Q  312

           GAGCCTCTCCACGTCGCGCAGGCGCTGCAGAAAGTGAAGATCGAGGTGAACGAGAGTGGC
    1081 ---------+---------+---------+---------+---------+---------+ 1140
           CTCGGAGAGGTGCAGCGCGTCCGCGACGTCTTTCACTTCTAGCTCCACTTGCTCTCACCG
aa         E  P  L  H  V  A  Q  A  L  Q  K  V  K  I  E  V  N  E  S  G  332

           ACGGTGGCCTCCTCATCCACAGCTGTCATAGTCTCAGCCCGCATGGCCCCCGAGGAGATC
    1141 ---------+---------+---------+---------+---------+---------+ 1200
           TGCCACCGGAGGAGTAGGTGTCGACAGTATCAGAGTCGGGCGTACCGGGGGCTCCTCTAG
aa         T  V  A  S  S  S  T  A  V  I  V  S  A  R  M  A  P  E  E  I  352

           ATCATGGACAGACCCTTCCTCTTTGTGGTCCGGCACAACCCCACAGGAACAGTCCTTTTC
    1201 ---------+---------+---------+---------+---------+---------+ 1260
           TAGTACCTGTCTGGGAAGGAGAAACACCAGGCCGTGTTGGGGTGTCCTTGTCAGGAAAAG
aa         I  M  D  R  P  F  L  F  V  V  R  H  N  P  T  G  T  V  L  F  372
```

FIGURE 1B

```
     ATGGGCCAAGTGATGGAACCCTGACCCTGGGGAAAGACGCCTTCATCTGGGACAAAACTG
1261 ---------+---------+---------+---------+---------+---------+ 1320
     TACCCGGTTCACTACCTTGGGACTGGGACCCCTTTCTGCGGAAGTAGACCCTGTTTTGAC
a a   M  G  Q  V  M  E  P  * 379

     GAGATGCATCGGGAAAGAAGAAACTCCGAAGAAAAGAATTTTAGTGTTAATGACTCTTTC
1321 ---------+---------+---------+---------+---------+---------+ 1380
     CTCTACGTAGCCCTTTCTTCTTTGAGGCTTCTTTTCTTAAAATCACAATTACTGAGAAAG

     TGAAGGAAGAGAAGACATTTGCCTTTTGTTAAAAGATGGTAAACCAGATCTGTCTCCAAG
1381 ---------+---------+---------+---------+---------+---------+ 1440
     ACTTCCTTCTCTTCTGTAAACGGAAAACAATTTTCTACCATTTGGTCTAGACAGAGGTTC

     ACCTTGGCCTCTCCTTGGAGGACCTTTAGGTCAAACTCCCTAGTCTCCACCTGAGACCCT
1441 ---------+---------+---------+---------+---------+---------+ 1500
     TGGAACCGGAGAGGAACCTCCTGGAAATCCAGTTTGAGGGATCAGAGGTGGACTCTGGGA

     GGGAGAGAAGTTTGAAGCACAACTCCCTTAAGGTCTCCAAACCAGACGGTGACGCCTGCG
1501 ---------+---------+---------+---------+---------+---------+ 1560
     CCCTCTCTTCAAACTTCGTGTTGAGGGAATTCCAGAGGTTTGGTCTGCCACTGCGGACGC

     GGACCATCTGGGGCACCTGCTTCCACCCGTCTCTCTGCCCACTCGGGTCTGCAGACCTGG
1561 ---------+---------+---------+---------+---------+---------+ 1620
     CCTGGTAGACCCCGTGGACGAAGGTGGGCAGAGAGACGGGTGAGCCCAGACGTCTGGACC

     TTCCCACTGAGGCCCTTTGCAGGATGGAACTACGGGGCTTACAGGAGCTTTTGTGTGCCT
1621 ---------+---------+---------+---------+---------+---------+ 1680
     AAGGGTGACTCCGGGAAACGTCCTACCTTGATGCCCCGAATGTCCTCGAAAACACACGGA

     GGTAGAAACTATTTCTGTTCCAGTCACATTGCCATCACTCTTGTACTGCCTGCCACCGCG
1681 ---------+---------+---------+---------+---------+---------+ 1740
     CCATCTTTGATAAAGACAAGGTCAGTGTAACGGTAGTGAGAACATGACGGACGGTGGCGC

     GAGGAGGCTGGTGACAGGCCAAAGGCCAGTGGAAGAAACACCCTTTCATCTCAGAGTCCA
1741 ---------+---------+---------+---------+---------+---------+ 1800
     CTCCTCCGACCACTGTCCGGTTTCCGGTCACCTTCTTTGTGGGAAAGTAGAGTCTCAGGT

     CTGTGGCACTGGCCACCCCTCCCCAGTACAGGGGTGCTGCAGGTGGCAGAGTGAATGTCC
1801 ---------+---------+---------+---------+---------+---------+ 1860
     GACACCGTGACCGGTGGGGAGGGGTCATGTCCCCACGACGTCCACCGTCTCACTTACAGG

     CCCATCATGTGGCCCAACTCTCCTGGCCTGGCCATCTCCCTCCCCAGAAACAGTGTGCAT
1861 ---------+---------+---------+---------+---------+---------+ 1920
     GGGTAGTACACCGGGTTGAGAGGACCGGACCGGTAGAGGGAGGGGTCTTTGTCACACGTA

     GGGTTATTTTGGAGTGTAGGTGACTTGTTTACTCATTGAAGCAGATTTCTGCTTCCTTTT
1921 ---------+---------+---------+---------+---------+---------+ 1980
     CCCAATAAAACCTCACATCCACTGAACAAATGAGTAACTTCGTCTAAAGACGAAGGAAAA

     ATTTTTATAGGAATAGAGGAAGAAATGTCAGATGCGTGCCCAGCTCTTCACCCCCCAATC
1981 ---------+---------+---------+---------+---------+---------+ 2040
     TAAAAATATCCTTATCTCCTTCTTTACAGTCTACGCACGGGTCGAGAAGTGGGGGGTTAG
```

FIGURE 1C

```
     TCTTGGTGGGGAGGGGTGTACCTAAATATTTATCATATCCTTGCCCTTGAGTGCTTGTTA
2041 ---------+---------+---------+---------+---------+---------+ 2100
     AGAACCACCCCTCCCCACATGGATTTATAAATAGTATAGGAACGGGAACTCACGAACAAT

     GAGAGAAAGAGAACTACTAAGGAAAATAATATTATTTAAACTCGCTCCTAGTGTTTCTTT
2101 ---------+---------+---------+---------+---------+---------+ 2160
     CTCTCTTTCTCTTGATGATTCCTTTTATTATAATAAATTTGAGCGAGGATCACAAAGAAA

     GTGGTCTGTGTCACCGTATCTCAGGAAGTCCAGCCACTTGACTGGCACACACCCCTCCGG
2161 ---------+---------+---------+---------+---------+---------+ 2220
     CACCAGACACAGTGGCATAGAGTCCTTCAGGTCGGTGAACTGACCGTGTGTGGGGAGGCC

     ACATCCAGCGTGACGGAGCCCACACTGCCACCTTGTGGCCGCCTGAGACCCTCGCGCCCC
2221 ---------+---------+---------+---------+---------+---------+ 2280
     TGTAGGTCGCACTGCCTCGGGTGTGACGGTGGAACACCGGCGGACTCTGGGAGCGCGGGG

     CCGCGCCCCCCGCGCCCCTCTTTTTCCCCTTGATGGAAATTGACCATACAATTTCATCCT
2281 ---------+---------+---------+---------+---------+---------+ 2340
     GGCGCGGGGGGCGCGGGGAGAAAAAGGGGAACTACCTTTAACTGGTATGTTAAAGTAGGA

     CCTTCAGGGGATCAAAAGGACGGAGTGGGGGACAGAGACTCAGATGAGGACAGAGTGGT
2341 ---------+---------+---------+---------+---------+---------+ 2400
     GGAAGTCCCCTAGTTTTCCTGCCTCACCCCCCTGTCTCTGAGTCTACTCCTGTCTCACCA

     TTCCAATGTGTTCAATAGATTTAGGAGCAGAAATGCAAGGGGCTGCATGACCTACCAGGA
2401 ---------+---------+---------+---------+---------+---------+ 2460
     AAGGTTACACAAGTTATCTAAATCCTCGTCTTTACGTTCCCCGACGTACTGGATGGTCCT

     CAGAACTTTCCCCAATTACAGGGTGACTCACAGCCGCATTGGTGACTCACTTCAATGTGT
2461 ---------+---------+---------+---------+---------+---------+ 2520
     GTCTTGAAAGGGGTTAATGTCCCACTGAGTGTCGGCGTAACCACTGAGTGAAGTTACACA

     CATTTCCGGCTGCTGTGTGTGAGCAGTGGACACGTGAGGGGGGGGTGGGTGAGAGAGACA
2521 ---------+---------+---------+---------+---------+---------+ 2580
     GTAAAGGCCGACGACACACACTCGTCACCTGTGCACTCCCCCCCCACCCACTCTCTCTGT

     GGCAGCTCGGATTCAACTACCTTAGATAATATTTCTGAAAACCTACCAGCCAGAGGGTAG
2581 ---------+---------+---------+---------+---------+---------+ 2640
     CCGTCGAGCCTAAGTTGATGGAATCTATTATAAAGACTTTTGGATGGTCGGTCTCCCATC

     GGCACAAAGATGGATGTAATGCACTTTGGGAGGCCAAGGCGGGAGGATTGCTTGAGCCCA
2641 ---------+---------+---------+---------+---------+---------+ 2700
     CCGTGTTTCTACCTACATTACGTGAAACCCTCCGGTTCCGCCCTCCTAACGAACTCGGGT

     GGAGTTCAAGACCAGCCTGGGCAACATACCAAGACCCCCGTCTCTTTAAAAATATATATA
2701 ---------+---------+---------+---------+---------+---------+ 2760
     CCTCAAGTTCTGGTCGGACCCGTTGTATGGTTCTGGGGGCAGAGAAATTTTTATATATAT

     TTTTAAATATACTTAAATATATATTTCTAATATCTTTAAATATATATATATATTTTAAAG
2761 ---------+---------+---------+---------+---------+---------+ 2820
     AAAATTTATATGAATTTATATATAAAGATTATAGAAATTTATATATATATATAAAATTTC

     ACCAATTTATGGGAGAATTGCACACAGATGTGAAATGAATGTAATCTAATAGAAGC
2821 ---------+---------+---------+---------+---------+------ 2876
     TGGTTAAATACCCTCTTAACGTGTGTCTACACTTTACTTACATTAGATTATCTTCG
```

| Mutaion # | Mutation | Nucleotide replacement | Parental multiple mutants selected from IEXlox library of random hPAI1 mutations |
|---|---|---|---|
| 1 | S331R | $T_{993}$-->A | mm1M, mm4M, mm3 & mm10 hPAI1 |
| 2 | K88E | $A_{262}$-->G | mm1 & mm3M hPAI1 |
| 3 | D89G | $A_{266}$-->G | mm5hPAI1 |
| 4 | G230V | $G_{689}$-->T | mm8hPAI1 |
| 5 | N87D | $A_{259}$-->G | mm9hPAI1 |
| 6 | N329I | $A_{986}$-->T | mm9hPAI1 |
| 7 | Q174R | $A_{521}$-->G | mm7hPAI1 |
| 8 | T232S | $A_{694}$-->T | mm7hPAI1 |

FIGURE 3

| Clone | Amino acid substitution | | | | | | Total substitutions | Active PAI-1, mg/L lysate | Active PAI-1, % of wt |
|---|---|---|---|---|---|---|---|---|---|
| cm9 | N87D | S308C | N329I | M354L | | | 4 | 2 | 4 |
| cm1m | R115W | S331R | | | | | 2 | 71 | 126 |
| cm4m | T339A | S331R | | | | | 2 | 50 | 90 |
| cm10 | D95G | S331R | L151M | M202K | I223V | S127T | 6 | 36 | 64 |
| cm3 | G218D | S331R | Y241C | | | | 3 | 55 | 97 |
| cm1 | K88E | R300K | S92C | S13T | | | 4 | 138 | 246 |
| cm3m | K88E | M110T | E212K | E283V | | | 4 | 100 | 178 |
| cm8 | G230V | D305V | E351G | | | | 3 | 3 | 6 |
| cm5 | D89G | H2L | V1E | T196S | | | 4 | 40 | 71 |
| cm7 | Q174R | T232S | | | | | 2 | 44 | 79 |
| hPAI-1 (wt) | N/A | N/A | N/A | N/A | N/A | N/A | 0 | 56 | 100 |

FIGURE 6

| Mutaion # | Mutation | Nucleotide replacement | Mutagenic primers |
|---|---|---|---|
| 1 | N87D | $A_{259}$-->G | 5' - ggA gCT CAT ggg gCC ATg ggA CAA ggA TgA gAT-3' |
| 2 | K88E | $A_{262}$-->G | 5'-gCT CAT ggg gCC ATg gAA CgA ggA TgA gAT CAg-3' |
| 3 | D89G | $A_{266}$-->G | 5'-CAT ggA ACA Agg gTg AgA TCA gC-3' |
| 4 | Q174R | $A_{521}$-->G | 5' gCC CTC TAC TTC AAC ggC Cgg Tgg AAg ACT CCC TTC CCC 3' |
| 5 | G230V | $G_{689}$-->T | 5' CTg AAC TgC CCT ACC Acg Tgg ACA CCC TCA gCA TgT TC 3' |
| 6 | T232S | $A_{694}$-->T | 5' - CCA Cgg ggA CTC CCT CAg CAT g - 3' |
| 7 | N329I | $A_{986}$-->T | 5' gTg AAg ATC gAg gTg ATC gAg AgT ggC Acg gTg 3' |
| 8 | S331R | $T_{993}$-->A | 5' - gTg AAC gAg AgA ggC ACg gTg - 3' |

SEQUENCE LISTING

```
<160> NUMBER OF SEQ ID NOS: 12

<210> SEQ ID NO 1
<211> LENGTH: 2876
<212> TYPE: DNA
<213> ORGANISM: Homo sapiens
<220> FEATURE:
<221> NAME/KEY: CDS
<222> LOCATION: (76)..(1281)

<400> SEQUENCE: 1

gaattcctgc agctcagcag ccgccgccag agcaggacga accgccaatc gcaaggcacc      60

tctgagaact tcagg atg cag atg tct cca gcc ctc acc tgc cta gtc ctg      111
                 Met Gln Met Ser Pro Ala Leu Thr Cys Leu Val Leu
                 1               5                   10

ggc ctg gcc ctt gtc ttt ggt gaa ggg tct gct gtg cac cat ccc cca       159
Gly Leu Ala Leu Val Phe Gly Glu Gly Ser Ala Val His His Pro Pro
        15                  20                  25

tcc tac gtg gcc cac ctg gcc tca gac ttc ggg gtg agg gtg ttt cag       207
Ser Tyr Val Ala His Leu Ala Ser Asp Phe Gly Val Arg Val Phe Gln
    30                  35                  40

cag gtg gcg cag gcc tcc aag gac cgc aac gtg gtt ttc tca ccc tat       255
Gln Val Ala Gln Ala Ser Lys Asp Arg Asn Val Val Phe Ser Pro Tyr
45                  50                  55                  60

ggg gtg gcc tcg gtg ttg gcc atg ctc cag ctg aca aca gga gga gaa       303
Gly Val Ala Ser Val Leu Ala Met Leu Gln Leu Thr Thr Gly Gly Glu
                65                  70                  75

acc cag cag cag att caa gca gct atg gga ttc aag att gat gac aag       351
Thr Gln Gln Gln Ile Gln Ala Ala Met Gly Phe Lys Ile Asp Asp Lys
            80                  85                  90

ggc atg gcc ccc gcc ctc cgg cat ctg tac aag gag ctc atg ggg cca       399
Gly Met Ala Pro Ala Leu Arg His Leu Tyr Lys Glu Leu Met Gly Pro
        95                  100                 105

tgg aac aag gat gag atc agc acc aca gac gcg atc ttc gtc cag cgg       447
Trp Asn Lys Asp Glu Ile Ser Thr Thr Asp Ala Ile Phe Val Gln Arg
    110                 115                 120

gat ctg aag ctg gtc cag ggc ttc atg ccc cac ttc ttc agg ctg ttc       495
Asp Leu Lys Leu Val Gln Gly Phe Met Pro His Phe Phe Arg Leu Phe
125                 130                 135                 140

cgg agc acg gtc aag caa gtg gac ttt tca gag gtg gag aga gcc aga       543
Arg Ser Thr Val Lys Gln Val Asp Phe Ser Glu Val Glu Arg Ala Arg
                145                 150                 155

ttc atc atc aat gac tgg gtg aag aca cac aca aaa ggt atg atc agc       591
Phe Ile Ile Asn Asp Trp Val Lys Thr His Thr Lys Gly Met Ile Ser
            160                 165                 170

aac ttg ctt ggg aaa gga gcc gtg gac cag ctg aca cgg ctg gtg ctg       639
Asn Leu Leu Gly Lys Gly Ala Val Asp Gln Leu Thr Arg Leu Val Leu
        175                 180                 185

gtg aat gcc ctc tac ttc aac ggc cag tgg aag act ccc ttc ccc gac       687
Val Asn Ala Leu Tyr Phe Asn Gly Gln Trp Lys Thr Pro Phe Pro Asp
    190                 195                 200

tcc agc acc cac cgc cgc ctc ttc cac aaa tca gac ggc agc act gtc       735
Ser Ser Thr His Arg Arg Leu Phe His Lys Ser Asp Gly Ser Thr Val
205                 210                 215                 220

tct gtg ccc atg atg gct cag acc aac aag ttc aac tat act gag ttc       783
Ser Val Pro Met Met Ala Gln Thr Asn Lys Phe Asn Tyr Thr Glu Phe
                225                 230                 235

acc acg ccc gat ggc cat tac tac gac atc ctg gaa ctg ccc tac cac       831
Thr Thr Pro Asp Gly His Tyr Tyr Asp Ile Leu Glu Leu Pro Tyr His
```

-continued

```
        240                 245                 250

ggg gac acc ctc agc atg ttc att gct gcc cct tat gaa aaa gag gtg      879
Gly Asp Thr Leu Ser Met Phe Ile Ala Ala Pro Tyr Glu Lys Glu Val
            255                 260                 265

cct ctc tct gcc ctc acc aac att ctg agt gcc cag ctc atc agc cac      927
Pro Leu Ser Ala Leu Thr Asn Ile Leu Ser Ala Gln Leu Ile Ser His
    270                 275                 280

tgg aaa ggc aac atg acc agg ctg ccc cgc ctc ctg gtt ctg ccc aag      975
Trp Lys Gly Asn Met Thr Arg Leu Pro Arg Leu Leu Val Leu Pro Lys
285                 290                 295                 300

ttc tcc ctg gag act gaa gtc gac ctc agg aag ccc cta gag aac ctg     1023
Phe Ser Leu Glu Thr Glu Val Asp Leu Arg Lys Pro Leu Glu Asn Leu
                305                 310                 315

gga atg acc gac atg ttc aga cag ttt cag gct gac ttc acg agt ctt     1071
Gly Met Thr Asp Met Phe Arg Gln Phe Gln Ala Asp Phe Thr Ser Leu
            320                 325                 330

tca gac caa gag cct ctc cac gtc gcg cag gcg ctg cag aaa gtg aag     1119
Ser Asp Gln Glu Pro Leu His Val Ala Gln Ala Leu Gln Lys Val Lys
        335                 340                 345

atc gag gtg aac gag agt ggc acg gtg gcc tcc tca tcc aca gct gtc     1167
Ile Glu Val Asn Glu Ser Gly Thr Val Ala Ser Ser Ser Thr Ala Val
    350                 355                 360

ata gtc tca gcc cgc atg gcc ccc gag gag atc atc atg gac aga ccc     1215
Ile Val Ser Ala Arg Met Ala Pro Glu Glu Ile Ile Met Asp Arg Pro
365                 370                 375                 380

ttc ctc ttt gtg gtc cgg cac aac ccc aca gga aca gtc ctt ttc atg     1263
Phe Leu Phe Val Val Arg His Asn Pro Thr Gly Thr Val Leu Phe Met
                385                 390                 395

ggc caa gtg atg gaa ccc tgaccctggg gaaagacgcc ttcatctggg            1311
Gly Gln Val Met Glu Pro
            400

acaaaactgg agatgcatcg ggaaagaaga aactccgaag aaaagaattt tagtgttaat   1371

gactctttct gaaggaagag aagacatttg ccttttgtta aaagatggta aaccagatct   1431

gtctccaaga ccttggcctc tccttggagg acctttaggt caaactccct agtctccacc   1491

tgagaccctg ggagagaagt ttgaagcaca actcccttaa ggtctccaaa ccagacggtg   1551

acgcctgcgg gaccatctgg ggcacctgct tccacccgtc tctctgccca ctcgggtctg   1611

cagacctggt tcccactgag gccctttgca ggatggaact acggggctta caggagcttt   1671

tgtgtgcctg gtagaaacta tttctgttcc agtcacattg ccatcactct tgtactgcct   1731

gccaccgcgg aggaggctgg tgacaggcca aaggccagtg gaagaaacac cctttcatct   1791

cagagtccac tgtggcactg gccacccctc cccagtacag gggtgctgca ggtggcagag   1851

tgaatgtccc ccatcatgtg gcccaactct cctggcctgg ccatctccct ccccagaaac   1911

agtgtgcatg ggttattttg gagtgtaggt gacttgttta ctcattgaag cagatttctg   1971

cttcctttta tttttatagg aatagaggaa gaaatgtcag atgcgtgccc agctcttcac   2031

cccccaatct cttggtgggg aggggtgtac ctaaatattt atcatatcct tgcccttgag   2091

tgcttgttag agagaaagag aactactaag gaaaataata ttatttaaac tcgctcctag   2151

tgtttctttg tggtctgtgt caccgtatct caggaagtcc agccacttga ctggcacaca   2211

cccctccgga catccagcgt gacggagccc acactgccac cttgtggccg cctgagaccc   2271

tcgcgccccc cgcgcccccc gcgcccctct ttttcccctt gatggaaatt gaccatacaa   2331

tttcatcctc cttcagggga tcaaaaggac ggagtggggg gacagagact cagatgagga   2391

cagagtggtt tccaatgtgt tcaatagatt taggagcaga aatgcaaggg gctgcatgac   2451
```

-continued

```
ctaccaggac agaactttcc ccaattacag ggtgactcac agccgcattg gtgactcact   2511

tcaatgtgtc atttccggct gctgtgtgtg agcagtggac acgtgagggg ggggtgggtg   2571

agagagacag gcagctcgga ttcaactacc ttagataata tttctgaaaa cctaccagcc   2631

agagggtagg gcacaaagat ggatgtaatg cactttggga ggccaaggcg ggaggattgc   2691

ttgagcccag gagttcaaga ccagcctggg caacatacca agacccccgt ctctttaaaa   2751

atatatatat tttaaatata cttaaatata tatttctaat atctttaaat atatatatat   2811

attttaaaga ccaatttatg ggagaattgc acacagatgt gaaatgaatg taatctaata   2871

gaagc                                                               2876


<210> SEQ ID NO 2
<211> LENGTH: 402
<212> TYPE: PRT
<213> ORGANISM: Homo sapiens

<400> SEQUENCE: 2

Met Gln Met Ser Pro Ala Leu Thr Cys Leu Val Leu Gly Leu Ala Leu
  1               5                  10                  15

Val Phe Gly Glu Gly Ser Ala Val His His Pro Pro Ser Tyr Val Ala
             20                  25                  30

His Leu Ala Ser Asp Phe Gly Val Arg Val Phe Gln Gln Val Ala Gln
         35                  40                  45

Ala Ser Lys Asp Arg Asn Val Val Phe Ser Pro Tyr Gly Val Ala Ser
     50                  55                  60

Val Leu Ala Met Leu Gln Leu Thr Thr Gly Gly Glu Thr Gln Gln Gln
 65                  70                  75                  80

Ile Gln Ala Ala Met Gly Phe Lys Ile Asp Asp Lys Gly Met Ala Pro
                 85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
    210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285
```

-continued

```
Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Ser Thr Ala Val Ile Val Ser Ala
        355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro


<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Mutagenic
      primer

<400> SEQUENCE: 3

ggagctcatg gggccatggg acaaggatga gat                                33


<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Mutagenic
      primer

<400> SEQUENCE: 4

gctcatgggg ccatggaacg aggatgagat cag                                33


<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Mutagenic
      primer

<400> SEQUENCE: 5

catggaacaa gggtgagatc agc                                           23


<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Mutagenic
      primer

<400> SEQUENCE: 6

gccctctact tcaacggccg gtggaagact cccttcccc                          39


<210> SEQ ID NO 7
<211> LENGTH: 38
<212> TYPE: DNA
```

-continued

<213> ORGANISM: Artificial Sequence
<220> FEATURE:
<223> OTHER INFORMATION: Description of Artificial Sequence: Mutagenic primer

<400> SEQUENCE: 7
ctgaactgcc ctaccacgtg gacaccctca gcatgttc 38

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Mutagenic primer

<400> SEQUENCE: 8
ccacggggac tccctcagca tg 22

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Mutagenic primer

<400> SEQUENCE: 9
gtgaagatcg aggtgatcga gagtggcacg gtg 33

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Mutagenic primer

<400> SEQUENCE: 10
gtgaacgaga gaggcacggt g 21

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ser Ala Val His His
1 5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Val His His Pro Pro
1 5

MUTANT PROTEINASE-INHIBITORS AND USES THEREOF

This application claims benefit of application Ser. No. 60/305,908 filed Jul. 18, 2001 now abandoned.

BACKGROUND OF THE INVENTION

1. Field of the Invention

The present invention relates to mutant proteinase inhibitors and fragments thereof, including serpins (serine proteinase inhibitors), particularly inhibitory serpins such as plasminogen activator inhibitors (PAIs), anti-thrombin III, and $\alpha_1$-antitrypsin ($\alpha_1$AT). The proteinase inhibitors in question comprise an amino acid sequence with at least one epitope in which a mutation has altered the binding of the mutant molecule to an anti-proteinase inhibitor antibody, relative to the binding of a corresponding wild-type molecule to the same antibody. The invention also relates to the use of a mutant proteinase inhibitor or fragment thereof for screening or designing proteinase inhibitor-inactivating agents or compounds that have potential as therapeutic agents to treat conditions associated with increased levels of proteinase inhibitors in vivo. The invention more broadly relates to the use of such technology to identify tertiary binding epitopes in metastable proteins that are not amenable to rational drug design screening, thereby to screen for and design inhibitor compounds or agents that have potential to reduce levels of such metastable proteins in the body.

2. Description of the Related Art

Considerable information is available on proteinase inhibitors and their ability to regulate many biologically important systems in the body. The influence of these inhibitors is based on their ability to regulate a variety of divergent proteinases. Particularly important proteinase inhibitors are serpins, a super family of inhibitors that apparently share a common tertiary structure, Doolittle (1983), *Science* 222: 417-419, and may have a common evolutionary ancestor. Hunt et al. (1980), *Biochem.Biophys-.Res.Comm.* 95:864-871. Proteins with recognizable sequence homology have been identified in vertebrates, plants, insects and viruses but not, thus far, in prokaryotes. Huber et al., (1989). *Biochem.* 28: 8951-8966; Sasaki (1991), *Eur.J.Biochem.* 202:255-261; Komiyama et al. (1994) *J.Biol. Chem.* 269: 19331-19337. Current models of serpin structure are based largely on seminal X-ray crystallographic studies of one member of the family, $\alpha_1$-antitrypsin ($\alpha_1$AT). Huber et al., (1989),. supra. Loebermann and co-workers solved the structure of a modified form of $\alpha_1$AT, cleaved in its reactive center, by proposing a model where the native reactive center is part of an exposed loop, also called the strained loop. See Loebermann et al., (1984). *J.Mol.Biol.* 177: 531-557; Carrell et al. In PROTEINASE INHIBITORS 403-20 (Elsevier Science Publishers, 1986); Sprang, S. R. (1992). *Trends Biochem.Sci.* 17: 49-50.

Recent crystallographic structures of several native serpins, with intact reactive center loops, are consistent with Loebermannø hypothesis that the overall native serpin structure is very similar to cleaved $\alpha_1$AT, but that the reactive center loop is exposed above the plane of the molecule. Schreuder et al., (1994) *Nature Structural Biology* 1: 48-54; Carrell et al. (1994) *Structure* 2: 257-270; Stein et al. (1990) *Nature* 347: 99-102; Wei et al., (1994) *Nature Structural Biology* 1: 251-258.; Sharp et al., (1999) *Structure* 7:111-118. Additional evidence has come from studies where synthetic peptides, homologous to the reactive center loops of $\alpha_1$AT, antithrombin III (ATIII), or plasminogen activator inhibitor-1 (PAI-1), when added in trans, incorporate into their respective molecules, presumably as a central strand of β-sheet A. Björk, et al. (1992), J.Biol.Chem. 267, 19047-19050; Björk, I. (1992), *J.Biol.Chem.* 267, 1976-1982; Schulze et al. (1990), *Eur. J. Biochem.* 194: 51-56; Carrell et al. (1991), *Nature* 317:730-732; Kvassman et al. (1995) *Bichem.* 37: 15491-15502. This leads to an increase in thermal stability similar to that observed following cleavage of a serpin at its reactive center, and converts the serpin from an inhibitor to a substrate for its target proteinase.

An additional serpin structural form has also been identified, the so-called latent conformation. In this structure the reactive center loop is intact, but instead of being exposed, the entire amino-terminal side of the reactive center loop is inserted as the central strand into β-sheet A. Mottonen et al. (1992) *Nature* 355:270-273. This accounts for the increased stability of latent PAI-1 (Lawrence et al.(1994b) *Biochem.* 33: 3643-3648), as well as its lack of inhibitory activity (Hekman et al. (1985) *J.Bio.Chem.* 260:11581-11587). The ability to adopt this conformation is not unique to PAI-1, and has also now been shown for ATIII and $\alpha_1$AT. Carrell et al. (1994), supra; Lomas et al. (1995) *J.Bio.Chem.* 270:5282-5288. Together, these data have led to the hypothesis that active serpins have mobile reactive center loops, and that this mobility is essential for inhibitor function. Carrell et al. (1991), supra; Carrell et al. (1992), *Curr.Opin.Struct.Biol.* 2: 438-446; Lawrence et al. (1994a) *J.Bio.Chem.* 269:27657-27662; Shore et al. (1994) *J.Bio.Chem.* 270:5395-5398; Lawrence et al. (1995) *J.Bio.Chem.* 270:25309-25312; Fa et al.(1995) *Biochem.* 34: 13833-13840; Olson et al. (1995) *J.Bio. Chem.* 270:30007-30017; Lawrence et al. (1990) *J.Bio.Chem.* 265:20203-20301.

An important member of the serpin super-family is plasminogen activator inhibitor (PAI). The PAIs have become recognized as critical regulators of the plasminogen activator (PA) system. The identification of an efficient inhibitor of t-PA in endothelial cells was first reported by Loskutoff et al., (1983) *Proc. Natl. Acad. Sci. USA* 80:2956-2960. Four kinetically relevant PAIs are recognized currently: PAI-1, initially described as the oendothelial cell PAI,p PAI-2, also referred to as oplacental PAI,p PAI-3, also known as oactivated protein C-inhibitor,p and proteinase nexin 1 (PN-1), also called oglia-derived neurite-promoting factor.p Recent interest has centered on PAI-1 because it plays an important role in fibrinolysis and is an established risk factor for cardiovascular disease. PAI-1 is the major plasminogen activator (PA) inhibitor in plasma and platelets. Booth et al., (1988) *Br.J.Haematol.* 70:327-333; Fay et al.(1992) *N.Engl-.J.Med.* 327:1729-1733; Fay et al.(1994) *Blood* 83:351-356.

The PAI-1 gene is 12.3 kb in length, and yields two mRNA species of 2 kb and 3 kb that both encode the same 50 kDa single-chain glycoprotein. Ny et al. (1986)) *Proc. Natl. Acad. Sci. USA* 83:6776-6780; Strandberg et al. (1988), *Eur. J. Biochem.* 176: 609-616; van Mourik et al. (1984) *J.Bio.Chem.* 259:14914-14921. PAI-1 is the most efficient inhibitor known of both uPA and tPA. Lawrence et al. (1989), *Eur. J. Biochem.* 186: 523-533; Sherman et al. (1992) *J.Bio.Chem.* 267:7588-7595.

PAI-1 exists in three interconvertible conformations: an active, a latent and a substrate form. The active conformation inhibits its target proteinases, tissue-type plasminogen activator (tPA) and urokinase-type plasminogen activator (uPA), by the formation of stable covalent complexes. The reactive site bond (P-P'$_1$) is inaccessible to the target proteinases in the latent form whereas the noninhibitory substrate form of PAI-1 is cleaved at the reactive site bond by the serine proteinases, resulting in an irreversible inactivation of PAI-1, and with the regeneration of the proteinase activity.

Active PAI-1 decays to the latent form with a half-life of approximately 1 hour at 37° C. With exposure to denaturants (guanidine HCl or SDS), latent PAI-1 can be returned partially to the active form. Though recent X-ray crystallographic findings suggest a structural basis for these two conformations (Mottonen et al. (1992), supra), their biological significance remains unknown. Negatively-charged phospholipids can convert latent PAI-1 to the active form, suggesting that cell surfaces may modulate PAI-1 activity Lambers et al. (1987) *J.Bio.Chem.* 262:17492-17496. The observation that latent PAI-1 infused into rabbits is apparently converted to the active form is consistent with this hypothesis Vaughan et al.(1990) *Cir.Res.* 67:1281-1286. Kinetic and other evidence has also been presented for a second site of interaction between PAI-1 and tPA, outside of the PAI-1 reactive center. Lawrence et al. (1990), supra; Hekman, et al. (1988). *Arch.Biochem.Biophys.* 262, 199-210.

PAI-1 plays an important role in the fibrinolytic system, in which it reduces the endogenous ability to remove fibrin by inhibiting plasminogen activators (PAs), such as tissue type PA (tPA) and urokinase-type plasminogen activator (uPA). Studies also have shown that elevations of PAI-1 are associated with increased risk for thromboembolic disease. Hamsten et al.(1985) *N. Engl. J. Med.* 313:1557-1563; Krishnamurti et al. (1992) *Semin. Thromb. Hemost.* 18:67-80; Schneiderman et al. (1992) *Proc. Natl. Acad. Sci. USA* 89:6998-7002. Therefore, inactivation of PAI-1 would potentially be of great therapeutic value. Levi et al. (1994) *Blood* 83: 351-356; Fay et al. (1995) *Circulation* 91: 1175-1181.

Strategies for reducing PAI activity in vivo fall into two basic categories. First, PAI-1 synthesis can be reduced directly through the action of drugs that depress PAI-1 gene expression. Second, PAI-1 activity can be blocked by specific antibodies or by pharmacological agents that act as specific inhibitors of PAI-1. Direct inactivators of PAI-1 have the potential for specifically reducing the total PAI-1 activity in plasma, and several recent reports demonstrated their efficacy. Levi et al., supra; Biemond et al. (1995) *Circulation* 91: 1175-1181; Stringer et al. (1994) *Arierioscler. Thromb.* 14: 1452-1458; Charlton et al. (1997) *Fibrinolysis & Proteolysis* 11: 51-56; Friderich et al. (1997) *Circulation* 96: 916-921; van Giezen et al. (1997) *Thromb. Haemost* 77: 964-969.

In the first studies to use this approach, PAI-1 activity was reduced by reaction with specific anti-PAI-1 monoclonal antibodies. Levi et al., supra; Biemond et al., supra; Stringer et al., supra; Debrock et al. (1997) *Biochim. Biophys. Acta* (1997) 1337:257-266; Debrock et al. (1997) *Gene* (1997) 189: 83-88. These studies demonstrate that anti-PAI-1 antibodies can be effective at neutralizing PAI-1 activity both in vitro and in vivo, and suggest that in circumstances when acutely high PAI-1 levels may be detrimental, such therapies may be useful, as for example, as an adjunct to thrombolytic therapy. Although antibody therapy looks promising, its long-term use is unlikely to be successful.

A related strategy for therapy that shows more promise is to prevent or at least influence reactive center loop insertion during PAI-1 interaction with PAs, and thereby prevent formation of the stable covalent complex. This method of blocking PAI-1 activity has been reported to occur in at least two different systems. In the first system, a synthetic peptide analogous to the reactive center loop of PAI-1 inserts into the β-sheet, and once there, it prevents the efficient insertion of the natural loop upon cleavage by a PA. Kvassman et al. (1995) *J. Biol. Chem.* 270: 27942-27947. As a consequence, PAI-1 is converted to a substrate for PAs, effecting an irreversible inactivation of PAI-1 by a PA. In a second study, a longer peptide of related sequence was also shown to inactivate PAI-1 Eitzman et al. (1995) *J. Clin. Invest.* 95:2416-2420. But this peptide seemed to induce a conformational change in PAI-1 that did not convert it to a substrate but instead to the non-inhibitory latent form.

Conventional technology has not afforded large scale and relatively simple methodology for selecting potentially effective compounds to treat cardiovascular disease and other pathological conditions that are characterized by elevated levels of a proteinase inhibitor, particularly PAI-1.

SUMMARY OF THE INVENTION

The present invention addresses the need to identify specific proteinase inhibitor inactivating agents by disclosing an assay that can be used to screen for them. This assay utilizes the recognition that specific antibodies bind to proteinase inhibitors, specifically serpins, more specifically PAIs, $\alpha_1$AT (Whisstock et al., (2000) *J. Mol. Biol.* 296(2): 685-699), and anti-thrombin III, (Larsson et al., (2000) *Cancer Res.* 60(23): 6723-6729), and most specifically PAI-1. This recognition led the present inventors to study proteinase inhibitors by mapping the epitopes to which specific anti-proteinase inhibitor antibodies bind. Locating these epitopes in the proteinase inhibitors and mutating these eptiopes results in the production of specific mutant proteinase inhibitors and fragments thereof that are used for the design and screening of compounds that inhibit specific proteinase inhibitors. The present disclosure provides an assay suitable for screening inhibitors of any metastable protein which cannot be studied using conventional methodology, such as a traditional epitope-identification screen that utilizes synthetic peptides, or a lambda gt11 phage screen or a protein crystal formation.

The present invention is directed to a mutant proteinase inhibitor comprising a wild-type proteinase inhibitor amino acid sequence with at least one mutation in at least one epitope of said amino acid sequence, wherein the mutation alters the binding of the mutant proteinase inhibitor to an anti-proteinase inhibitor antibody as compared to the binding of the wild-type proteinase inhibitor to the anti-proteinase inhibitor antibody.

The present invention is additionally directed to a fragment of the mutant proteinase inhibitor, wherein the fragment comprises at least one mutation in at least one epitope of the amino acid sequence of a wild-type proteinase inhibitor fragment.

The present invention further is directed to a nucleic acid sequence comprising a nucleotide construct encoding the mutant proteinase inhibitor or a fragment of the mutant proteinase inhibitor comprising at least one mutation in at least one epitope of the amino acid sequence.

The present invention additionally is directed to a vector and host transformed or transfected with the nucleic acid construct or vector comprising the nucleic acid sequence or construct encoding the mutant proteinase inhibitor or a fragment of the mutant proteinase inhibitor comprising at least one mutation in at least one epitope of the amino acid sequence.

The present invention further is directed to a method for producing a mutant proteinase inhibitor or a fragment thereof comprising culturing the host transformed or trans fected with the nucleic acid construct or vector comprising the nucleic acid sequence or construct encoding the mutant proteinase inhibitor or a fragment thereof, under conditions wherein said nucleic acid sequence is expressed.

The present invention is further directed to a method of screening at least one compound that affects the activity of a proteinase inhibitor. The method is directed to screening for at least one compound by comparing the extent of binding of the compound to the mutant proteinase inhibitor or the fragment thereof to the binding to the wild-type proteinase inhibitor or fragment thereof.

The present invention is additionally directed to a method of screening at least one compound that affects the activity of a proteinase inhibitor, particularly the inhibitory activity of the proteinase inhibitor. The method is directed to screening for at least one compound that has less of an effect or no effect on the inhibitory activity on the inhibitory activity of the mutant proteinase inhibitor or the fragment thereof as compared to the effect on the inhibitory activity of the wild-type proteinase inhibitor or fragment thereof.

In a further embodiment, the present invention is additionally directed to a method of mapping compound binding sites in a metastable protein by comparing the effect of the compound on a measurable activity of the mutant metastable protein of fragment thereof to the measurable activity of the wild-type metastable protein or fragment thereof.

BRIEF DESCRIPTION OF THE DRAWINGS

FIGS. 1*a*-1*d* show the nucleotide sequence (SEQ ID NO: 1) encoding human PAI-1 with 5' and 3' untranslated regions from a specific clone. Also shown is the amino acid sequence (SEQ ID NO: 2) of the full length human PAI-1 including the signal sequence.

FIG. 2 provides a list of specific site-directed mutations generated in the human PAI-1 molecule in order to map the MA-33B3 monoclonal antibody binding site on human PAI-1.

FIG. 3 provides a table summarizing 11 independent human PAI-1 clones showing the observed amino acid substitutions in the amino acid sequence shown in FIG. 1 and corresponding functional activity of these mutant clones.

FIG. 6 shows eight site-directed mutations (SEQ ID NOS: 3-10, respectively) that were constructed to create PAI-1 variants that are specifically defective in binding of the monoclonal antibody 33B8, along with the specific nucleotide replacements made and the mutagenic primers used to introduce these replacements.

DETAILED DESCRIPTION OF THE PREFERRED EMBODIMENT

Figure 4:
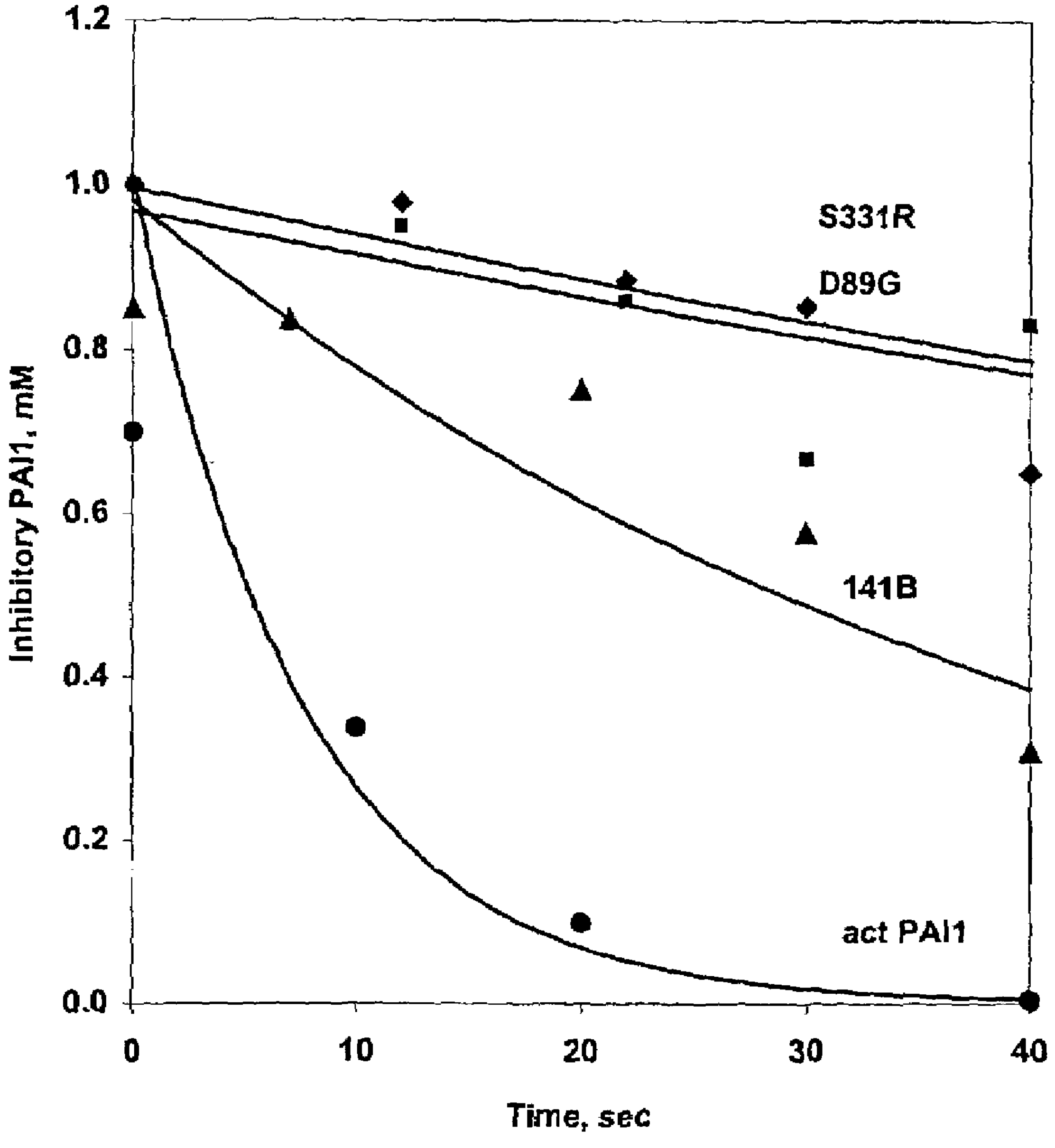
FIG. 4 is MA-33B8-induced inactivation of wild-type and mutant human PAI-1. ≦=wild-type PAI-1; ñ=141B; ·=S331R and ↿=D89G

The present invention embodies an approach to screening for compounds that bind to or affect the activity of metastable proteins. In this context, a ometastablep protein is an unstable protein that is not amenable to co-crystallization with a compound, followed by a determination of the coordinates of this binding event. Thus, a metastable protein is not readily subject to rational drug design. A metastable protein within the meaning of the present invention and to persons skilled in the art is a protein that is folded into a conformation that is not its most thermodynamicly stable conformation.

Representing an advance over known epitope-identification techniques, the approach of the present invention maps the binding site(s) by screening for loss of antibody binding to specific members within libraries of mutants of metastable proteins. This binding may be determined by some measurable activity possessed by the wild-type metastable protein or its mutant. Mutants that lose only their ability to bind to the antibody, and not other functions of the wild-type metastable protein, identify the binding site(s) as encompassing the various amino acid residues that are present only in these specific mutants.

Accordingly, the present invention encompasses screening compounds for the ability to inhibit a protein that is metastable and, hence, cannot be put through a typical rational drug-design regimen, involving co-crystallization with the compound. One class of such proteins includes proteinase inhibitors, such as the serpins, including $\alpha_1$ATs, antithrombins, and PAIs, particularly PAI-1. In accordance with the present invention, therefore, one can design and prepare mutants of proteinase inhibitors (that is, full-length proteins and biologically active fragments thereof) in light of information gleaned from binding studies between wild-type proteinase inhibitors and antibodies specific for proteinase inhibitors.

The drug screening approach of the present invention exploits the changes (mutations) in the mutant proteinase inhibitors to identify compounds that bind less strongly to, that inactivate to a lesser degree, or that cannot inactivate the mutant proteinase inhibitors, but that bind more strongly to, that can inactivate to a greater degree, or that can inactivate wild-type proteinase inhibitor. For example, there are multiple potential binding sites for compounds on PAI-1. If a single, specific compound effects wild type PAI-1 inhibition activity but cannot inhibit the mutant PAI-1, then it is reasonable to conclude that the compound is binding at the mutated site in the PAI-1. From this information, additional compounds can be designed based upon the structure of this oinactivep molecule. Thus, rationale drug design accordingly to the present invention can proceed without having the protein crystallized. Moreover, while the present description discusses PAI-1 as a representative metastable protein, the aforementioned drug-screening methodology has impact outside of the PAI-1 field.

The activity measured as a result of the interaction of the mutant protein must be compared to the activity of the corresponding wild-type protein interaction with the compound. For example with PAI-1, it is inherent in the assay that both the mutant and wild type PAI-1 have equivalent inhibitory activity against the target proteinase, prior to mixing the PAI-1 with the compound. Alternatively, control runs can be performed to take into account any differences in inhibitory activity of the mutant and wild-type PAI-1s.

A mutant proteinase inhibitor obtained according to the present invention can be used in screening for and designing compounds to affect proteinase inhibitors in vivo, thereby to realize therapeutic potential in treating diseases that involve elevated proteinase-inhibitor levels. Such mutant proteinase inhibitors also can be employed to identify specific antibodies or other binding epitopes that are tertiary in nature and not revealed by traditional epitope identification techniques, which utilize synthetic peptides or a lambda gt11 phage screen or which require protein crystal formation.

To develop a reliable screen for metastable proteins, the inventors have drawn from their expertise with a serpin, PAI-1, and the binding interaction between PAI-1 and anti-PAI antibodies. Specifically, the inventors measured the binding between mutant and wild-type PAI-1 and anti-PAI antibodies, and compared the extent of binding of the anti-PAI antibodies to mutant and wild-type PAI-1s. The inventors observed that certain PAI-1 mutants lost their ability to bind (or they bound at a reduced level) to an anti-PAI-1 antibody, relative to binding to and inactivation of wild-type PAI-1. For the disclosed method to function as a viable screen, all that is necessary is that this relative binding between the mutant and wild-type PAI-1s be measurable. Further, the method of screening can also be based on measuring some activity of the metastable protein, PAI-1. Preferably, PAI-1 inhibitory activity against its target proteinase is the activity that is measured, following contact with anti-PAI antibodies but any other measurable activity of PAI-1 can be used in the screening method.

Another embodiment of the present invention relates to PAI-1 mutants that contain one or more epitope mutations, relative to a corresponding wild-type PAI-1, that are involved in binding an anti-PAI antibody. The key to the screening method of the present invention is that the mutation(s) in the PAI-1 mutant are used to identify a compound that binds less strongly to the mutant PAI-1 than the same compound binds to the corresponding wild-type PAI-1. This wild-type PAI-1 contains the same amino acid sequences as the mutant PAI-1 except that the epitope to which the anti-PAI antibody binds in the wild-type PAI-1 is modified to contain one or more changes, such as a substitution, a deletion and/or an addition of at least one amino acid that make up the epitope. The epitope is modified to produce mutant PAI-1s of the present invention. Although the present invention encompasses any modification of the epitope(s) in the mutant PAI-1, amino acid substitutions in the epitope are preferred. The mutants are prepared according to the present invention and are tested for activity and binding to anti-PAI antibodies, thereby to determine their utility in the screening method. In this regard, the term oepitopep connotes a specific site of interaction or binding between two molecules, and it generally takes on an immunological definition to describe, for example, the binding between an anti-PAI antibody and a mutant or wild-type PAI-1, where the definition of an epitope is the antigenic determinant on an antigen to which the paratope, the specific site within an antibody Fab region, binds.

The screening method of the present invention can measure binding to the mutant and wild-type PAI-1s of compounds that are to be screened. The extent of binding between compounds and the mutant and wild-type PAI-1s are compared and compounds that bind less to the mutant PAI-1 than to the wild-type PAI-1 are selected as potential compounds that affect the inhibitory activity of PAI-1.

More particularly, the mutant PAI-1s are used in a screening method for evaluating compounds for their effect on mutant and wild-type PAI-1 activity. A compound that has potential as a PAI-1 inhibitory compound affects mutant PAI-1 activity less than it affects the wild-type PAI-1 activity. The PAI-1 activity that is measured is preferably PAI-1ø inhibitory activity against its target proteinase, and therefore the screening method preferably measures the effect on the PAI-1 inhibitory activity of the mutant PAI-1 as compared to the effect on the PAI-1 inhibitory activity of the wild-type PAI-1. More particularly, compounds that do not affect or inactivate the mutant PAI-1 activity but do affect to a greater extent or inactivate the corresponding wild-type PAI-1 are compounds that the screening method is designed to identify. The most preferred compounds that are identified by this method are those compounds that do not bind to the mutant proteinase inhibitor or a fragment thereof but do bind to the wild-type proteinase inhibitor or a fragment thereof.

There are multiple potential binding sites for compounds on PAI-1. If a specific compound inhibits the wild-type PAI-1 but cannot inhibit the mutant PAI-1, then the compound binding site must be the mutated epitope to which the specific compound binds.

From this information, additional compounds are designed to bind to the wild-type PAI-1 based upon the structure of the compound that is inactive against the mutant PAI-1. For example, if the identified epitope of the anti-PAI-1 antibody overlaps with a binding pocket for one or more compounds, such as compounds that inactivate PAI-1, then the PAI-1 mutants disclosed in the present invention provide a useful screen for PAI-1 inactivating agents.

Additionally, the screening method of the present invention is useful for identifying specific antibodies or other binding epitopes that are tertiary in nature, and therefore, refractive to traditional epitope identification screens, such as those using synthetic peptides or a lambda gtl 1 phage screen. Further, the screening method is useful to identify other proteins that may bind differentially to mutant PAI-1s.

The present invention also is directed to a method of screening at least one compound that affects the activity of a metastable protein, which by definition is unstable and not amenable to rational drug design. The method also is useful for mapping compound binding sites in a metastable protein.

Thus, in one embodiment the present method comprises (a) incubating a compound separately with: (i) a mutant metastable protein or a fragment thereof, and (ii) a wild-type metastable protein or a fragment thereof; (b) measuring the effect of the compound in (a) on a measurable activity of the mutant metastable protein or a fragment thereof and the wild-type metastable protein or fragment thereof; and (c) comparing the effect of the compound in (b) on the measurable activity of the mutant metastable protein or the fragment with the effect of the compound on the measurable activity of the wild-type metastable protein or the fragment thereof. When the compound affects the measurable activity of the wild-type stable protein, the method further comprises: (d) selecting a compound that has less of an effect on the activity of the mutant metastable protein or the fragment thereof in (b) than the effect on the activity of the wild-type stable protein or the fragment.

More specifically, the present invention is directed to a method of mapping at least one compound binding site in a metastable protein or fragment thereof comprising: (a) incubating a mutant metastable protein or fragment thereof with a compound; (b) measuring the effect of the compound in (a) on a measurable activity of the mutant metastable protein; (c) performing a parallel set of steps (a') and (b') comprising the same steps as (a) and (b), except that the wild-type metastable protein is substituted for the mutant metastable protein in step (a'); (d) comparing the effect of the mutant metastable protein in (b) and the wild-type metastable protein in (b'); and (e) selecting a compound that has less of an effect on the measruable activity of the mutant metastable protein or fragment thereof in (b) than the effect on the measurable activity of the wild-type metastable protein or fragment in (b').

The inventive screening method also may entail control treatments comprising: (f) performing a parallel set of steps (a'') through (d'') corresponding to steps (a) through (d) and performing a parallel set of steps (a''') through (d''') corresponding to steps (a') through (d'), except that no compound is added in step (a) or (a'); and (g) comparing the measurable activity of the mutant metastable protein in (b) and (b'') and the wild-type metastable protein in (b') and (b''') to determine the relative effect on a measurable activity of the mutant metastable protein and the wild-type metastable protein.

The method further comprises performing a control incubation, wherein the measurable activity is measured without the addition of the mutant metastable protein or the wild-type metastable protein in (a) and (a'), described above. The method further comprises performing a control incubation, wherein the measurable activity is measured without the addition of the mutant metastable protein, the wild-type metastable protein or the compound in (a) and (a'). The method additionally comprises a mutant metastable protein or a fragment thereof that is prepared by introducing at least one mutation in at least one epitope of the amino acid sequence of said wild-type metastable protein or a fragment thereof, wherein the mutation alters the binding of the mutant metastable protein or fragment thereof to an antibody that binds to the wild-type metastable protein or fragment thereof.

A mutant metastable protein or fragment thereof, used in the method described above, is prepared by introducing at least one mutation in at least one epitope of the amino acid sequence of the wild-type metastable protein or fragment thereof, wherein the mutation alters the binding of the mutant metastable protein or fragment thereof to an antibody that binds to a greater extent to the wild-type metastable protein or fragment thereof than to the mutant metastable protein.

The mutant metastable protein or fragment thereof of the present invention retains from about 5 j 100% of its measurable activity in the presence of the compound, and more preferably retains at least about 25% of its measurable activity in the presence of the compound. More preferably the mutant metastable protein or fragment thereof of the present invention retains at least about 50% of its measurable activity in the presence of the compound, and more preferably retains at least about 75% of its measurable activity in the presence of the compound. Most preferably the compound has substantially no effect on the inhibitory activity of the mutant metastable protein or fragment thereof, and the metastable protein. The retention of measurable activity as indicated above were measured in the presence of the compound.

The present invention is more preferably directed to a method of screening at least one compound that affects the activity of a proteinase inhibitor comprising: (a) incubating a compound with: (i) a mutant proteinase inhibitor as described herein or a fragment thereof, wherein the inhibitor or the fragment comprises at least one mutation in at least one epitope of the amino acid sequence; and separately incubating the compound with (ii) a wild-type proteinase inhibitor or a fragment thereof; (b) measuring the binding of the mutant proteinase inhibitor or the fragment and the wild-type proteinase inhibitor or the fragment with the compound; and (c) comparing the binding of the compound to the mutant proteinase inhibitor or the fragment with the binding of the compound to a wild-type proteinase inhibitor or the fragment. The method further comprises: (d) selecting a compound that binds less strongly with the mutant proteinase inhibitor or the fragment thereof as compared to the binding of the compound to the wild-type proteinase inhibitor or the fragment.

A compound that binds to the mutant proteinase inhibitor or the fragment thereof about 95% or less than the binding of the compound to the wild-type proteinase inhibitor or fragment thereof is preferred, and a compound that binds to the mutant proteinase inhibitor or the fragment thereof about 75% or less than the binding of the compound to the wild-type proteinase inhibitor or fragment thereof is more preferred. A compound that binds to the mutant proteinase inhibitor or the fragment thereof about 50% or less than the binding of the compound to the wild-type wild-type proteinase inhibitor or fragment thereof is more preferred, and a compound that binds to the mutant proteinase inhibitor or the fragment thereof about 24% or less than the binding of the compound to the wild-type proteinase inhibitor or fragment thereof is more preferred. But a compound that does not bind to the mutant proteinase inhibitor or the fragment thereof but does bind to the wild-type proteinase inhibitor or the fragment thereof is most preferred.

In addition to screening compounds by measuring binding of the compound to the mutant and wild-type proteinase inhibitors, the method of screening further can measure the effect of at least one compound on a measurable activity of a proteinase inhibitor. In this aspect, the method comprises: (a) incubating a compound with: (i) a mutant proteinase inhibitor comprising a wild-type mutant proteinase inhibitor amino acid sequence with at least one mutation in at least one epitope of the amino acid sequence, wherein the mutation alters the binding of the mutant proteinase inhibitor to an anti-proteinase inhibitor antibody as compared to the binding of the wild-type proteinase inhibitor to the anti-proteinase inhibitor antibody or a biologically active fragment of the mutant proteinase inhibitor, wherein the inhibitor or the fragment comprises at least one mutation in at least one epitope of the amino acid sequence; and separately incubating the compound with: (ii) a wild-type proteinase inhibitor or a fragment thereof; (b) measuring the effect of the compound in (a) on the inhibitory activity of the mutant proteinase inhibitor or the fragment thereof and the wild-type proteinase inhibitor or the fragment thereof; and (c) comparing the effect of the compound on the mutant proteinase inhibitor or the fragment thereof with the effect of the compound on a wild-type proteinase inhibitor or the fragment. When the compound affects the inhibitory activity of the wild-type proteinase, the method further comprises: (d) selecting a compound that has less of an effect on the inhibitory activity of the mutant proteinase inhibitor or the fragment in (b) than the effect on the inhibitory activity of the wild-type proteinase inhibitor or the fragment.

Mutant proteinase inhibitors and fragments thereof that retain from about 5-100% of its inhibitory activity in the absence of the compound is also useful in the present invention, and mutant proteinase inhibitors and fragments thereof that retain at least about 25% of its inhibitory activity is more preferred. But mutant proteinase inhibitors and fragments thereof that retain at least about 50% of its inhibitory activity is more preferred, and mutant proteinase inhibitors and fragments thereof that retain at least about 24% of its inhibitory activity is more preferred. The most preferred compounds that are identified by this method are those compounds that have no inhibitory effect on the mutant proteinase inhibitor or a fragment thereof but do inhibit the wild-type proteinase inhibitor or a fragment thereof, where the mutant proteinase inhibitor or fragment thereof retains 100% of its inhibitory activity. The retention of the inhibitory activity of the mutant proteinase inhibitor or fragment thereof against its target proteinase as indicated above is measured in the absence of the compound.

More preferably, the method of the present invention comprises screening compounds that affects a mutant proteinase inhibitor comprising: (a) incubating a mutant proteinase inhibitor comprising a wild-type proteinase inhibitor amino acid sequence with at least one mutation in at least one epitope of the amino acid sequence, wherein the mutation alters the binding of the mutant proteinase inhibitor to an anti-proteinase inhibitor antibody as compared to the binding of the wild-type proteinase inhibitor to the anti-proteinase inhibitor antibody or a fragment thereof with a compound; (b) measuring the effect of the compound in (a) on the inhibitory activity of the mutant proteinase inhibitor on a target proteinase; (c) performing a parallel set of steps (a') and (b') comprising the same steps as (a) and (b), except that wild-type proteinase inhibitor is substituted for the mutant proteinase inhibitor in step (a'); (d) comparing the effect on the inhibitory activity of the mutant proteinase inhibitor in (b) and the wild-type proteinase inhibitor in (b'), and (e) selecting a compound that has less of an effect on the inhibitory activity of the mutant proteinase inhibitor in (b) than on the wild-type proteinase inhibitor in (b').

In regard to the measuring of step (b) and (b'), the method more preferably comprises adding a target proteinase to the mutant proteinase inhibitor and the compound of (a) to form a first mixture and to the wild-type proteinase inhibitor and the compound of (a') to form a second mixture and incubating the first and second mixtures. The measuring of (b) and (b') comprises measuring the target proteinase activity that comprises adding a substrate of the target proteinase and measuring the enzymatic conversion of the substrate.

The method of screening further comprises control treatments comprising: performing a parallel set of steps (a") through (d") corresponding to steps (a) through (d) and performing a parallel set of steps (a'") through (d'") corresponding to steps (a') through (d'), except that no compound is added in step (a") or (a'"); and (g) comparing the inhibitory activity of the mutant proteinase inhibitor in (b) and (b") and the wild-type proteinase inhibitor in (b') and (b'") to determine the relative inhibitory activity of the mutant proteinase inhibitor and the wild-type proteinase inhibitor. The method further comprises the measuring step of (b") and (b'") comprises adding a target proteinase to the mutant proteinase inhibitor of (a") to form a third mixture and to the wild-type proteinase inhibitor of (a'") to form a fourth mixture, and incubating the third and fourth mixtures. The method, wherein the measuring step of (b") and (b'") comprises measuring the target proteinase activity, comprises adding a substrate of the target proteinase and measuring the enzymatic conversion of the substrate.

The method further comprises performing a control incubation, wherein the target proteinase activity is measured without the addition of the mutant proteinase inhibitor or the wild-type proteinase inhibitor in (a) and (a').

The method further comprises performing a control incubation, wherein the target proteinase activity is measured without the addition of the mutant proteinase inhibitor,the wild-type proteinase inhibitor and/or the compound in (a) and (a').

The present invention is directed to the mutants that are used in the compound screening method(s) of the present invention. The mutant proteinase inhibitors of the present invention comprises a wild-type proteinase inhibitor amino acid sequence with at least one mutation in at least one epitope of the wild-type proteinase inhibitor amino acid sequence or a fragment thereof, wherein the mutation alters the binding of the mutant proteinase inhibitor to an anti-proteinase inhibitor antibody as compared to the binding of the wild-type proteinase inhibitor to the anti-proteinase inhibitor antibody.

Preferably, the mutant proteinase inhibitor has a lower binding affinity to the antibody than the anti-proteinase inhibitor antibody has for the wild-type proteinase inhibitor. More preferably, the mutant proteinase inhibitor antibody does not bind to the mutated epitope of the mutated proteinase inhibitor.

The mutant proteinase inhibitor is a mutant of the wild-type plasminogen activator inhibitor (PAI), and more preferably is a mutant of wild-type PAI-1. Most preferably, the mutant proteinase inhibitor comprises the amino acid sequence of the wild-type PAI depicted in FIG. 1.

A suitable anti-proteinase inhibitor antibody preferably is a monoclonal antibody that does not inhibit the mutant proteinase inhibitor or fragment thereof and does inhibit the wild-type proteinase inhibitor or fragment thereof. More preferably, the antibody is an anti-PAI monoclonal antibody, and more preferably an anti-PAI-1 monoclonal antibody. The most preferred anti-PAI monoclonal antibody includes but is not limited to murine monoclonal antibodies, MA-33B8 or 31C9, available commercially from Molecular Innovations, Inc. (Southfield, Mich.). However, any antibody that inhibits a measurable activity of the mutant proteinase inhibitor can be used, in accordance with the present invention, for identifying compounds that have potential to inhibit proteinase inhibitors.

The mutant proteinase inhibitor of the present invention comprises the amino acid sequence of FIG. 1*a*-1*d*, wherein the amino acid sequence comprises a substitution at one or more amino acid residues selected from the group consisting of 1, 2, 13, 82, 87, 88, 89, 92, 95, 110, 115, 127, 151, 174, 196, 202, 212, 218, 223, 230, 241, 283, 300, 305, 308, 329, 331, 323, 339, 351 and 354. More preferably the mutant proteinase inhibitor comprises a substitution at one or more amino acid residues selected from the group consisting of 87, 88, 89, 174, 230, 232, 329 and 331. FIG. 2 discloses a table setting forth specific amino acid substitutions at these amino acid residues and FIG. 3 discloses a table setting forth PAI-1 mutants of the present invention that contain multiple substitutions.

More preferably, the mutant proteinase inhibitor of the present invention comprises at least one amino acid substitution at amino acid 87, and more preferably the amino acid substitution at amino acid 87 is changing an asparagine to an aspartic acid. The designation for such a substitution is N87D, with the wild-type amino acid recited before the amino acid number and the substituted or changed amino acid recited after the amino acid number. Additionally, another preferred mutant proteinase inhibitor comprises at least one amino acid substitution at amino acid 89, wherein the amino acid substitution at amino acid 89 is changing an aspartic acid to glycine, D89G. Another preferred mutant proteinase inhibitor comprises at least one amino acid substitution at amino acid 230, wherein the amino acid substitution at amino acid 230 is changing a glycine to a valine, G230V. Another mutant proteinase inhibitor comprises at least one amino acid substitution at amino acid 331, wherein the amino acid substitution at amino acid 331 is changing a serine to an arginine, S331R.

The present invention also encompasses a fragment of the mutant proteinase inhibitor described above. The term ofragmentp is intended to be a portion of the mutant or wild-type proteinase inhibitor that is less than the full length of the proteinase inhibitor. It is important that the fragment comprises at least one mutation in at least one epitope of the amino acid sequence and it is important that when using the mutant proteinase inhibitor fragment in the screening method that its inhibitory activity be compared to the corresponding wild-type proteinase inhibitor fragment up to full-length wild-type proteinase inhibitor.

The present invention is further directed to a nucleic acid sequence comprising a nucleotide sequence encoding the mutant proteinase inhibitors described herein or a fragment of the mutant proteinase inhibitor comprising at least one mutation in at least one epitope of the amino acid sequence. The nucleic acid sequence preferably encodes a mutant of the wild-type plasminogen activator inhibitor (PAI), and more preferably is a mutant of wild-type PAI-1. Most preferably, the nucleic acid sequence encodes the mutant proteinase inhibitor comprising the amino acid sequence of the wild-type PAI depicted in FIG. 1.

The present invention also is directed to a nucleic acid construct comprising the nucleic acid sequence as described above operably linked to regulatory control sequences that effect the expression of the nucleic acid sequence. The present invention further comprises a vector comprising a nucleotide sequence encoding the mutant proteinase inhibitors described herein or a fragment of the mutant proteinase inhibitor comprising at least one mutation in at least one epitope of the amino acid sequence. The present invention is further directed to a host transformed or transfected with a nucleic acid construct of a nucleic acid sequence comprising a nucleotide sequence encoding the mutant proteinase inhibitors described herein or a fragment of the mutant proteinase inhibitor comprising at least one mutation in at least one epitope of the amino acid sequence as described above.

The mutant proteinase inhibitor or a fragment thereof of the present invention is produced by culturing a host comprising a nucleic acid sequence operably linked to regulatory control sequences that effect the expression of the nucleic acid sequence under conditions wherein said nucleic acid sequence is expressed.

To prepare mutants of wild-type proteins, a skilled person needs to know the amino acid and DNA sequences of the protein that is to be mutated.

In the case of the preferred protein, PAI-1 cDNA encodes a protein of 402 amino acids that includes a typical secretion signal sequence (Ny et al., 1986; Ginsburg et al., 1986). Mature human PAI-1 isolated from cell culture is composed of two variants of 381 and 379 amino acids in approximately equal proportions. These two forms, likely arising from alternative cleavage of the secretion signal sequence, provide proteins with overlapping amino-terminal sequences of Ser-Ala-Val-His-His (SEQ ID NO: 11) and Val-His-His-Pro-Pro (SEQ ID NO: 12) (see FIG. 1 and disclosed in Lawrence et al., 1989). This latter sequence is generally referred to as mature PAI-1. The complete amino acid and nucleotide sequence of PAI-1 also is disclosed in FIGS. 1*a*-1*d* showing that the amino acid sequence including the 23 amino acid signal sequence is 402 amino acids in length and the mature amino acid sequence is 379 amino acids.

PAI-1 is a glycoprotein with three potential N-linked glycosylation sites containing between 15 and 20% carbohydrate (Van Mourik et al., 1984). Mature PAI-1 contains no cysteine residues, facilitating efficient expression and isolation of recombinant PAI-1 from *E. coli*. PAI-1 produced in *E. coli*, although nonglycosylated, is functionally very similar to native PAI-1. Recombinant PAI-1 purified from mammalian cell culture (Lawrence et al., 1989; Hekman et al., 1988).

U.S. Pat. No. 6,103,498 discloses how to make modified PAI-1s or PAI-1 mutants and these methods are useful for preparing the mutant PAI-1s of the present invention, and is incorporated herein by reference in its entirety. Site-directed mutagenesis and other methods are used to produce and characterize a large number of mutations in the PAI-1 reactive center loop (RCL) (Sherman et al., 1992, Sherman et al., 1995). Although this previous patent application discloses how to make and identify new mutants in the RCL of PAI-1 which confer on PAI-1 new and useful properties, in particular (a) the ability to interact with and inhibit elastase, an activity which is lacking in native PAI-1 and (b) the ability to inhibit vitronectin-associated cell migration, it does not suggest preparing the mutant PAI-1s for use in the screening method of the present invention.

While the present disclosure is directed primarily to human PAI-1 or mutants thereof, it is to be understood that homologues of PAI-1 from other species, and mutants thereof, that possess the characteristics disclosed above are intended within the scope of this invention. In particular, the PAI-1 protein (or DNA) from other mammalian species may be used for the same purposes as human PAI-1 in the method of the present invention.

As noted above, the PAI-1 of the present invention can be produced recombinantly in *E. coli* or other host cells, or other known methods of producing proteins from DNA sequences, including the use of transgenic plants or animals using methods known to persons skilled in the art. The present invention also includes peptides that include at least that portion of the sequence which contains the substitution or substitutions, and which possess the requisite biochemical and biological activity. Such peptides are produced using well-known synthetic methods for the synthesis of polypeptides of desired sequence on solid phase supports and their subsequent separation from the support. Methods for solid phase peptide synthesis are well-described, for example, by: Merrifield, (1963); Merrifield, (1986); Wade, et al., (1986); Fields, (1990); MilliGen Report Nos. 2 and 2a (1987). For example, the otBoc methodp or an improved oF-mocp technique may be used (Atherton, et al., 1981).

EXAMPLES

Production of PAI-1 Mutants by Expression and Purification of Recombinant PAI-1 in *E. coli*

The following methods are preferred and do not represent the exclusive means for producing proteinase inhibitor mutants of the invention. Techniques for synthesizing oligonucleotide probes are well known in the art and disclosed by, for example, Wu, et al., 1978 or Gait, ed., (Current Edition). Procedures for constructing and expressing recombinant molecules in accordance with this invention, including appropriate promoters and other control elements, selection markers, etc., are disclosed by Sambrook, J. et al, 1989; Ausubel, F. M. et al., 1987, which references are herein incorporated by reference.

Included in this invention is the DNA encoding the PAI-1 mutants, which is preferably a cDNA having the appropriate nucleotide sequence substitutions to encode the mutant proteins as disclosed herein. Such molecules are prepared using conventional methods. Also included herein are prokaryotic or eukaryotic host cells transformed or transfected with a vector comprising the above DNA molecule. Again, the method used for transferring the DNA, expressing the DNA and growing the host cells are well-known in the art and described in the references cited above. Eukaryotic host cells are preferably mammalian cells of an established cell line, although insect cells or plant cells are also contemplated. Appropriate vectors such as viruses, vector sequences, control sequences, such as promoters appropriate for the species of host cells, are conventional and well-known to those skilled in the art and are therefore not described in particular detail herein. In addition to sense DNA, antisense DNA and antisense RNA molecules to the mutant PAI-1 coding sequence are provided herein. Also included is an RNA molecule encoding the PAI-1 mutant.

Example 1

Materials

The murine anti-human PAI-1 monoclonal antibodies (mAbs) 33B8 and 31C9, as well as rabbit anti-human PAI-1 polyclonal antibodies (pAbs) were obtained from Molecular Innovations (Southfield, Mich., USA). High molecular weight tPA and uPA were obtained from Genetech (South San Francisco, Calif.) and Molecular Innovations (Southfield, Mich., USA), respectively. Chromogenic tPA substrate pGlu-Gly-Arg p-nitroanilide was purchased from Sigma (St. Louis, Mo., USA). Nitrocellulose filters and membranes used for protein transfer were from Schleicher & Schuell, Inc. (Keene, N.H., USA). All supplies and reagents for SDS-PAGE including precast gels were from Novex (San Diego, Calif. USA). All *E. coli* strains used for subdloning, replication or expression of human PAI-1 wild-type or mutated genes were purchased from Stratagene (La Jolla, Calif. USA), Clontech Laboratories, Inc. (Palo Alto, Calif. USA) and Novagen (Madison, Wis., USA) as competent cells. For site-directed mutagenesis the Transformer™ Site-Directed Mutagenesis Kit was purchased from Clontech Laboratories, Inc. (Palo Alto, Calif. USA). All sequencing and mutagenic primers used were synthesized and PAGE purified by Integrated DNA Technologies, Inc. (Coralville, Iowa, USA). DNA restriction endonucleases (Sca I and Mlu I) were purchased from Life Technologies (Gaithersburg, Md., USA) and New England Biolabs, Inc.(Beverly, Ma., USA), respectively. DNA sequencing was done with the BlgDye™ Terminator Cycle Sequencing Ready Reaction Kit from Applied Biosystems (Foster City, Calif. USA) on ABI PRISM™ 310 Genetic Analyzer. Analysis of DNA sequences was performed with the Vector NTI™ Suite 6.0 Molecular Biology Software for Windows™. All supplies and buffers for binding assays with BIAcore 3000™ Biosensor were purchased from Biacore AB (Uppsala, Sweden). Bovine serum albumin (BSA), sodium azide ($NaN_3$), isopropyl thio-β-D-galactoside (IPTG), carbanicilin, tetracyclin and kanamycin were from Sigma (St. Louis, Mo., USA). All other chemical reagents used in the study were purchased from Fisher Scientific (Pittsburg, Pa., USA)., Construction and Screening of Mutant PAI-1 Library A library of random PAI-1 mutants with $>2\times10^7$ independent clones was constructed in the λ phage expression vector λEXlox by error-prone PCR as described in Berkenpas et al., 1995, incorporated by reference. Briefly, the entire coding sequence of mature PAI-1 was amplified by four cycles of error-prone PCR, as described by Lawrence et al., *J. Biol. Chem.* (1994) 269: 16223-16228, incorporated in its entirety by reference. The mutagenized product was gel purified from the template and re-amplified using standard PCR conditions to produce an amplified pool of randomly mutagenized PAI-1 cDNAs. The PCR product was cleaved with XbaI and EcoRI, ligated to similarly restricted λEXlox arms, and packaged with PhagePrep from Novagen (Madison, Wis., USA).

Lawns of phage-infected *Escherichia coli* BL21(DE3) were prepared from exponentially grown cells in Luria broth (LB) with 0.02% maltose. To select phage plaques with mutated PAI-1 molecules, protein expression was induced by incubating pregrown phage plaques with overlaid IPTG (10 mM)+tPA(10 g/ml) saturated nitrocellulose filters within 1 hr at 37° C. Lifted filters were once washed in TBS containing 0.5% SDS thoroughly then blocked with 1% BSA/5% milk/TBS solution and incubated with 33B8 mAbs, as a primary antibodies. Filter-bound tPA:PAI-1:33B8 mAbs complexes were detected immunologically with goat anti-mouse immunoglobulins, conjugated to horse radish peroxidase (HRP) in enhanced chemiluminescence (ECL)assay. The dark spots revealed on ECL Hyperfilms indicated plaques expressing PAI-1 molecules capable of binding to the 33B8 mAbs. Then filters were washed with water and TBS several times, incubated with rabbit anti-PAI-1 pAbs as the primary and goat anti-rabbit alkaline phosphatase (AP) conjugated antibodies as secondary ones. The dark purple spots appeared on the filters after NBT/BCIP color reaction corresponded to plaques expressing all functionally active PAI-1 molecules. To select 33B8 binding-negative plaques, the ECL Hyperfilms were overlapped with the original NBT/BCIP developed nitrocellulose filters. Plaques expressing 33B8 mAbs binding-negative phenotype were picked up from relevant bacterial plates and run through two sequential rounds of enrichment, which included the same steps as the primary screening.

Totally, three hundred thousand of λEXlox particles from L5 random mutations of h PAI-1 library were screened, and from 22 particles expressing active PAI-1 phenotype which were picked up in the first screen only 11 appeared to be positive after following two screens, and thus were isolated, automatically subdloned by Cre-mediated excision of plasmid DNA from λEXlox vector in accordance with Novagen (Madison, Wis., USA) protocol and subjected to further analysis.

DNA sequence analysis of entire PAI-1 coding region (1137 nucleotides) in 10 independent pEXmutPAI-1 plasmids demonstrated a mutational frequency of 1:366, resulting in an average of approximately three amino acid substitutions per variant.

Site-directed Mutagenesis

Site-directed mutagenesis allows the production of peptide variants through the use of specific oligonucleotide sequences that encode the DNA sequence of the desired mutation plus a sufficient number of adjacent mucleotides to provide a primer sequence of sufficient size and sequence complexity to form a stable duplex on both sides of the deletion junction being traversed. Typically, a primer of about 20 to 30 nucleotides in length is preferred, with about 5 to 10 residues on both sides of the junction of the sequence being altered. The technique of sitedirected mutagenesis is well known to persons skilled in the art, as exemplified by publications, such as Adelman et al., *DNA* 2:183 (1983), incorporated herein by reference.

The individual PAI-1 site-directed mutants were constructed by following the protocol from TransformerTm Site-Directed Mutagenesis Kit from Clontech Laboratories, Inc. (Palo Alto, Calif. USA) but other similar kits may be used to construct the mutants. The primers used in the protocol are designed using the PAI-1 DNA sequence provided in FIG. 1 and the known mutations identified in the initial screening of the library for clones that did not bind the 33 BA monoclonal antibody as described herein. Specific mutagenicp primers that were used to introduce desired mutations into the PAI-1 DNA sequence are disclosed in FIG. 6.

After final transformation in *E.coli* XL-10 Gold competent cells from Stratagene (La Jolla, Calif. USA) with the mutated PAI-1 DNA sequences, several clones of each individual mutant (at least four) were selected and sequenced throughout the entire PAI-1 coding region with 3-5 sequencing primers. Eventually, eight of the site-directed mutants, with the single amino acid replacement in positions 87, 88, 89, 174, 230, 232, 329 and 331 of PAI-1 molecule were constructed and evaluated as disclosed herein.

Functional Analysis of PAI-1 Molecules

Multiple 33B8-binding negative and single amino acid replacement hPAI-1 mutated genes as well as wild-type one were cloned in pEX plasmids and expressed in *E.coli* BL21 (DE3) Tuner strain from Novagen (Madison, Wis., USA). The cell-free lysates were prepared from cells pregrown to $OD_{600}$=0.5 O.U. and induced by IPTG (1 mM) within following 2 hrs. Pellets from 1.5 ml cultural medium were resuspended in 0.4 ml of 0.05 M KPi buffer (pH 5.1), containing 0.001 M EDTA, 0.15 M NaCl and 0.02% $NaN_3$, then sonicated for 1 min in 50% pulse regime with cooling using Ultrasonic processor XL (Misonix Inc., Farmingdale, N.Y.). Supernatant fractions, obtained after homogenates centrifugation for 15 minutes at 14,000 rpm, were denoted as cell-free extracts (CE) and used in PAI-1 activity assays. An aliquot of wild-type PAI-1 and each of mutant CEs, in serial dilutions from 1:40 up to 1:2560 in 0.05 M Tris HCl, pH 7.5 buffer, containing 0.15 M NaCl, 0.01% BSA, 0.0001% Tween 20, 0.02% SA, were analyzed for functional activity as measured by inhibitory activity against high molecular weight uPA using the single step chromogenic substrate assay as described (Lawrence et al. 1989 *Eur. J. Biochem*. 186: 529-539; Berkenpas et al.,1995). In addition, tPA inhibitory activity of mutant PAI-1 forms was evaluated by the direct formation of tPA:PAI-1 complex after 20 min of equimolar amounts tPA and PAI-1 incubation at 37° C. The reaction mixtures were analyzed by SDS-PAGE in 4-20% Tris-Glycine gradient gels under reducing conditions with prestained Sea Blue protein markers as a standards and followed by Coomassie Brilliant Blue-250 staining of the protein bands.

Binding Assays

Western Blot Assays

To evaluate the 33B8-binding-negative phenotype of selected PAI-1 mutants, an aliquots of CEs of *E.coli* BL21 (DE3)Tuner containing at least 5 ng of recombinant h PAI-1 were separated by SDS PAGE under reducing conditions; electro transferred to nitrocellulose membrane, blocked with 1% BSA/5% milk/TBS solution then probed with murine 33B8 mAbs and rabbit anti-h PAI-1 pAbs as the primary antibodies. The formed complexes were detected with HRP-conjugated goat anti-mouse or goat anti-rabbit immunoglobulins by ECL method according with the same procedure as for library screening (described above).

Surface Plasmon Resonance

The binding of purified h PAI-1 mutant proteins and *E. coli* BL21(DE3)Tuner CEs to specific murine anti-h PAI-1 33B8 mAbs has been also analyzed by surface plasmon resonance (SPR) method, using BIAcore™ 3000 optical Biosensor (BiacoreAB,Uppsala, Sweden). This method detects binding interactions in real time by measuring changes in the refractive index at a biospecific surface, enabling the association and dissociation rate constants to be calculated. Typically, 33B8 mAbs were coupled to a NHS/EDC-activated CM-5 research grade sensor chip flow cells, to yield approximately 1000 resonance units (RU) response. Individually, wild-type h PAI-1 in its active, latent, cleaved and complexed with uPA/tPA conformational forms as well as the single amino acid replacement and multiple mutant h PAI-1 proteins (0.001 j 1 μM ) in HBS-P buffer pH 7.4 were injected for 5 min at a flow rate of 20 μl/min followed by 10 min dissociation. Regeneration of the sensor chip surface was done with pulse of 20 μl 0.2 M Glycine buffer pH 1.5. All measurements-were performed at 25° C. BIAcore 3000 Bioevaluation Software (Biacore AB, Uppsala, Sweden) program package was used for analysis of data and affinity constants calculations.

Figure 5:
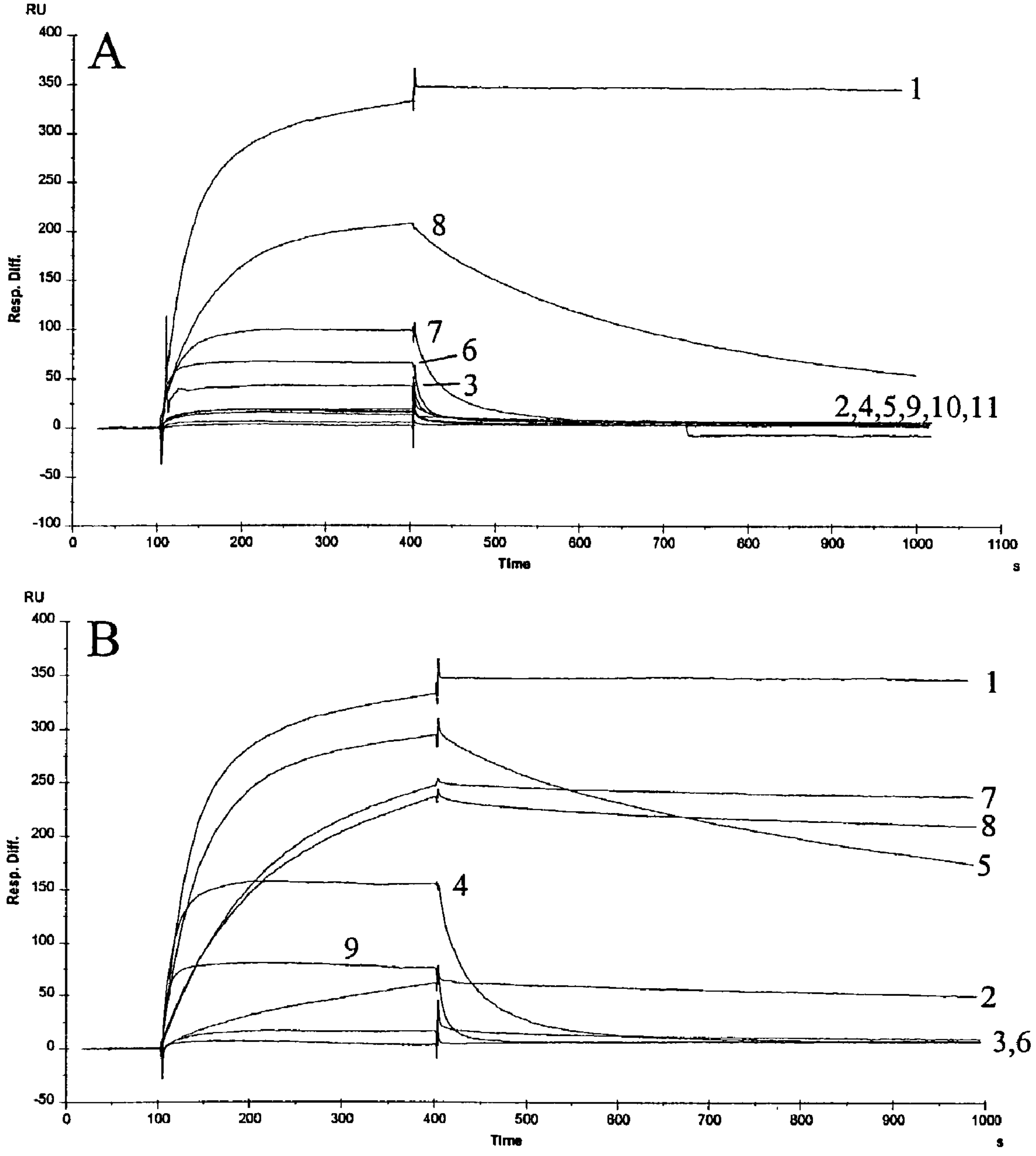
FIG. 5 shows the real-time binding of multiple (A) and site-directed (B) hPAI-1 mutants to inactivating murine monoclonal 33B8 antibodies measured with BIAcore 3000 biosensor. Murine monoclonal 33B8 antibodies were immobilized on research grade chip CM5 (BIAcore) by amine coupling method. Samples of *E.coli* cell-free extracts in HBS-P buffer pH 7.4 (BIAcore) containing 62 nM active PAI-1 were injected in HBS-P buffer at flow rate 20 μl/minute. The association and dissociation were observed in real time over period of 5 minutes. Panel A: 1-wt hPAI-1; 2-mm1; 3-mm1M; 4-mm3; 5-mm3M; 6-mm4M; 7-mm5; 8-mm7; 9-mm8; 10-mm9; 11-mm10. Panel B: 1-wt hPAI-1; 2-N87Dsdm; 3-K88Esdm; 4-D89Gsdm; 5-Q174Rsdm; 6-G230Vsdm; 7-T232Ssdm; 8-N329Isdm; 9-S331Rsdm.

The identified mutants of PAI-1 that did not bind to the 33B8 antibody with high affinity and also were not inactivated by 33B8. This is shown in FIG. 5: antibody MA-33B8 (2.33 mN) was preincubated with purified wild type and mutant recombinant hPAI1 (1 mM at room temperature) after which the residual PAI-1 activity was measured at the intervals indicated. These data indicate that both wild-type PAI-1, and the previously identified mutant of PAI-1, 14-1b (Lawrence et al. 1989 *Eur. J. Biochem*. 186: 529-539; Berkenpas et al.,1995), are both rapidly inactivated by the antibody. In contrast, two of the newly constructed single point mutations that were identified in the screen and are shown in FIG. 2 (S331R and D89G) are not rapidly inactivated by 33B8. This demonstrates that mutations that disrupt binding of 33B8 to PAI-1 also prevent 33B8 for rapidly inactivating the PAI-1.

Method for Determining the Effect of Inhibition of PAI-1 Mutant Activity by Novel Chemical Entities Novel chemical entities (NCE) are added at various concentrations to a buffer containing the PAI-1 mutant. Following mixing and incubation at room temperature, the target protease, either tissue plasminogen activator (tPA) or urokinase plasminogen activator (uPA), is added, and the combination of NCE, PAI-1 mutant and tPA/uPA is further incubated at room temperature. Following the second mixing and incubation, a chromogenic substrate for tPA/uPA is added and absorbance read in a spectrophometer at various times. Relative PAI-1 inhibitory activity is equal to the residual tPA/uPA activity in the NCE/mutant PAI-1 treatment compared to the activity in the presence of the mutant alone. By comparing these data to similar data generated by substituting wild-type PAI-1 for mutant PAI-1 in the presence of the NCE, the relative affinity of the NCE for the unique epitope within the mutant PAI-1 can be determined. Control treatments include the absence of any effect of the NCE on tPA/uPA activity alone. Only those compounds that have shown inhibitory activity against wild-type PAI-1 are further tested against mutant PAI-1. The inhibitory activity of the NCE against wild-type PAI-1 is determined by using a range of concentrations of the NCE, and estimating the molar concentration required for a 50% inhibitory effect using standard pharmacologic analysis. Under the conditions of the assay, those compounds ranked in the top 25% of all compounds tested are preferred, although compounds ranked from 26-75% may also have utility.

More specifically, Compound A, a NCE, is mixed with wild-type PAI-1 and produces a 100% reduction of the action of PAI-1 on uPA. Compound B, also a NCE, is mixed with wild-type PAI-1 and also produces a 100% reduction in the action of PAI-1 on uPA. Compound A is mixed with mutant PAI-1 S331R which results in a 50% reduction in the action of this mutant on uPA. Compound B is mixed with mutant PAI-1 S331R resulting in a 0% reduction of the inhibitory action of the mutant PAI-1on uPA. The complete absence of a reduction of the action of the Compound B on mutant PAI-1 S331R indicates that Compound B does not bind mutant PAI-1 S331R, while the 50% reduction in the action of Compound A on mutant PAI-1 S331R indicates that Compound A binds mutant PAI-1 S331R. The binding site for Compound B is identified by the amino acid substitution in mutant PAI-1 S331R, which correspond to the binding epitope in MA33B8 for PAI-1.

This example could be expanded to include other mutations or binding sites. Compounds of interest for binding to the MA33B8 epitope in PAI-1 would either exhibit 50-100% reduction, 25-49% reduction, or 0-24% reduction in the action of mutants of PAI-1 on uPA. Those compounds with 0-24% reduction in the action of PAI-1 mutants on uPA would be considered as exhibiting activity.

This example includes but is not restricted to uPA as the target protease for PAI-1. By the same token, this example is not restricted in its significance to PAI-1 and mutants of PAI-1, as the metastable protein targeted for compound binding. Range in percent reduction in action of compounds on PAI-1 for determination of activity is given for the purpose of illustration, and may vary.

Compounds identified via the inventive screening methodology are inhibitors of PAI-1 and, hence, are useful in the treating, inhibiting, preventing or prophylaxis of processes, in a mammal, preferably a human, that involve the production and/or action of PAI-1. Thus, a compound of the present invention may be useful:

in the treatment or prevention of non-insulin dependent diabetes mellitus;

in the prevention of thrombotic events associated with coronary artery and cerebrovascular disease;

in the inhibiting of a disease process involving thrombotic and prothrombotic states, including but not limited to the formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery, such as joint replacement, and peripheral arterial occlusion;

in the treatment of diseases associated with extracellular matrix accumulation, including but not limited to chronic obstructive pulmonary disease, polycystic ovary syndrome, restenosis, renovascular disease, and organ transplant rejection;

in the treatment of malignancies and diseases associated with neo-angiogenesis, such as diabetic retinopathy;

in conjunction with and following processes or procedures that maintain or that may affect blood vessel patency, including vascular surgery, vascular graft and stent patency, and organ, tissue and cell implantation and transplantation.

in the treatment of inflammatory diseases, septic shock and the vascular damage associated with infections;

in treatment of blood and blood products used in dialysis and blood storage in the fluid phase, especially ex vivo platelet aggregation;

during the analysis of blood chemistry in hospital settings, when the compound is added to human plasma, to determine the fibrinolytic capacity thereof;

in combination with prothrombolytic, fibrinolytic and anticoagulant agents;

in the treatment of cancers, including but not limited to breast and ovarian cancer, and, as an imaging agent, in the identification of metastatic cancers;

in the treatment of myelofibrosis, with myeloid metaplasia, by regulating stromal cell hyperplasia and effecting increases in extracellular matrix proteins;

in conjunction with protease inhibitor-containing, highly active anti-retroviral therapy (HAART), for the treatment of diseases, e.g., in HIV-1 infected patients receiving such therapy, that derive from fibrinolytic impairment and hyper-coagulability; and in the treatment of diabetic nephropathy and renal dialysis associated with nephropathy.

More generally, the compounds of the present invention find use in improving coagulation homeostasis and in treating septicemia, obesity, insulin resistance, psoriasis and other proliferative diseases, cerebrovascular diseases, microvascular disease, hypertension, dementia, osteoporosis, arthritis, asthma, heart failure, arrhythmia, and angina. An inventive compound also can be employed as a hormone replacement agent, for example, in treating, preventing, or reversing progression of atherosclerosis, osteoporosis, and osteopenia. It also can be employed for reducing inflammatory markers, reducing C-reactive protein, and preventing or treating low grade vascular inflammation, stroke, dementia and coronary heart disease, as well as in primary and secondary prevention of myocardial infarction, stable and unstable angina, in primary prevention and secondary prevention of cardiovascular events, in ameliorating peripheral vascular disease, peripheral arterial disease, acute vascular syndromes, in reducing the risk of undergoing a myocardial revascularization procedure, in treating microvascular diseases, such as nephropathy, neuropathy, retinopathy and nephrotic syndrome, hypertension, Type I and 2 diabetes and related diseases, hyperglycemia, hyperinsulinemia, malignant lesions, premalignant lesions, gastrointestinal malignancies, liposarcomas and epithelial tumors, and all forms of cerebrovascular diseases, and in improving endothelial function.

The compounds of the present invention also are useful in the treatment of Alzheimer's disease. This approach can be characterized, in accordance with the invention, as a method for increasing or normalizing plasmin levels in a subject, particularly one who is experiencing or who is subject to risk for Alzheimer's disease.

All of the publications and patent documents cited herein are incorporated in their entirety by reference.

We claim:

1. A nucleic acid sequence comprising a nucleotide sequence encoding a PAI-1 protein with at least one mutation in at least one epitope of said PAI-1 protein or a fragment of said PAI-1 protein comprising said mutation, wherein said mutation comprises at least one amino acid substitution selected from the group consisting of:

(a) Asp at positions 87;

(b) Glu at position 88;

(c) Gly at position 89;

(d) Arg at position 174;

(e) Val at position 230;

(f) Ser at position 232;

(g) Ile at position 329; and (h) Arg at position 331.

2. A nucleic acid construct comprising the nucleic acid sequence according to claim 1 operably linked to regulatory control sequences that effect the expression of said nucleic acid sequence.

3. A vector comprising the nucleic acid construct according to claim 2.

4. A host cell transformed or transfected with a nucleic acid construct according to claim 2.

* * * * *